(12) United States Patent
Khvorova et al.

(10) Patent No.: US 6,225,063 B1
(45) Date of Patent: May 1, 2001

(54) RNA CHANNELS IN BIOLOGICAL MEMBRANES

(75) Inventors: Anastasia Khvorova; Michael Yarus, both of Boulder, CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/315,886

(22) Filed: May 20, 1999

Related U.S. Application Data
(60) Provisional application No. 60/086,492, filed on May 22, 1998.

(51) Int. Cl.[7] .......................... C12Q 1/68; G01N 33/566; C07H 21/04

(52) U.S. Cl. ........................ 435/6; 436/501; 536/23.1

(58) Field of Search ................................ 435/6; 436/501, 436/829; 536/23.1

(56) References Cited

U.S. PATENT DOCUMENTS

| | | |
|---|---|---|
| 4,093,607 | 6/1978 | Sela et al. . |
| 4,657,760 | 4/1987 | Kung et al. . |
| 4,683,195 | 7/1987 | Mullis et al. . |
| 4,683,202 | 7/1987 | Mullis . |
| 4,965,188 | 10/1990 | Mullis et al. . |
| 5,149,794 | 9/1992 | Yatvin et al. . |
| 5,206,344 | 4/1993 | Katre et al. . |
| 5,225,212 | 7/1993 | Martin et al. . |
| 5,270,163 | 12/1993 | Gold et al. . |
| 5,475,096 | 12/1995 | Gold et al. . |
| 5,714,383 | 2/1998 | Thompson . |
| 5,728,818 | 3/1998 | Wincott et al. . |
| 5,795,778 | 8/1998 | Draper . |
| 5,795,782 * | 8/1998 | Church et al. ........................... 436/2 |
| 5,811,300 | 9/1998 | Sullivan et al. . |
| 5,869,253 | 2/1999 | Draper . |
| 5,877,022 | 3/1999 | Stinchcomb et al. . |
| 5,891,684 | 4/1999 | Usman et al. . |

FOREIGN PATENT DOCUMENTS

| | | |
|---|---|---|
| WO 97/38134 | 10/1997 | (WO) . |
| WO 98/33941 | 8/1998 | (WO) . |
| WO 99/07724 | 2/1999 | (WO) . |

OTHER PUBLICATIONS

Johansessen et al. Changes in distribution on actin mRNA in different polysome fractions following stimulation of MPC–11 cells. Mol. and Cellular Biochem. vol. 142:107–115, Jan. 1995.*

Bezlepkin et al. Formation of additional contacts of chromosome with membrane in the process of DNA repair synthesis in bacterial cells. Zeitschrift fur Allgemeine Mikrobilogie vol. 23(10):607–619, Feb. 1983.*

Campana et al. *Escherichia coli* mut T1 II: Consequences of modification on hte association of DNA with the cell membrane. Bionchimica et Biophysica Acta. vol. 563:17–27, Jan. 1979.*

Jayaraman, S. Localization of (dA–dT)–rich sequences in the membrane–bound DNA and their possible role in sporulation in *Bacillus polymyxa*. Mol. Gen. Genet. vol. 185(1):158–164, Jun. 1982.*

Yang et al. The physical mechanism of the close–packing of membrane–bound DNA in solution. Biophys. J. Vo.. 70 (2 part 2) p. A370, Feb. 1996.*

Anderson and Young, "Quantitative Filter Hybridization," in *Nucleic Acid Hybridization*, pp. 73–111 [1985].

Bartel et al., "Isolation of New Ribozymes from a Large Pool of Random Sequences," Science 261:1411–1418 [1993].

Beaudry et al., "Directed Evolution of an RNA Enzyme," Science 257:635–641 [1992].

Binkley et al., "RNA ligands to human nerve growth factor," Nucl. Acids Res., 23:3198–3205 [1995].

Bretscher, "Membrane Structure: Some General Principles," Science 181:622–629 [1973].

Budker et al., "Polynucleotides Adsorb on Mitochondrial and Model Lipid Membranes in the Presence of Bivalent Cations," FEBS Lett., 95:143–146 [1978].

Budker et al., "Interaction of polynucleotides with natural and model membranes," Nucl. Acids Res., 8:2499–2514 [1980].

Budker et al., "Cell membranes as barriers for antisense constructions," Anti. Res. Dev., 2:177–184 [1992].

Burke et al., "Recombination, RNA evolution, and bifunctional RNA molecules isolated through Chimeric SELEX," RNA 4:1165–1175 [1998].

Cech, "Ribozymes and Their Medical Implications," J. Amer. Med. Assoc., 260:3030–3034 [1988].

Chamberlin et al., "New RNA Polymerase from *Escherichia coli* Infected with Bacteriophage T7," Nature 228:227–231 [1970].

Ciesiolka et al., "Affinity Selection–Amplification from Randomized Ribooligonucleotide Pools," Meth. Enzymol., 267:315–335 [1996].

Connell et al., "Three Small Ribooligonucleotides with Specific Arginine Sites," Biochemistry 32:5497–5502 [1994].

(List continued on next page.)

*Primary Examiner*—Robert A. Schwartzman
*Assistant Examiner*—William Sandals
(74) *Attorney, Agent, or Firm*—Medlen & Carroll, LLP

(57) ABSTRACT

The present invention provides nucleic acid molecules capable of binding phospholipid membranes, and more particularly RNA molecules capable of binding and forming channels in biological membranes. In this regard the present invention provides methods for screening nucleic acid molecules that bind phospholipid membranes. The present invention also provides compositions of nucleic acid molecules capable of binding phospholipid membranes, as well as methods employing these compositions to alter the permeability or detectably label phospholipid membranes.

30 Claims, 7 Drawing Sheets

OTHER PUBLICATIONS

Connell et al., "RNAs with Dual Specificity and Dual RNAs with Similar Specificity," Science 264:1137–1141 [1994].

Davies et al., "Antibiotics and the RNA World: A Role for Low–molecular–weight Effectors in Biochemical Evolution?" Gesteland and Atkins (eds.), *The RNA World, The Nature of Modern RNA Suggests a Prebiotic RNA World*, pp. 185–204, Cold Spring Harbor Press, NY [1993].

Erlich (ed.), PCR Technology, Stockton Press [1989] (Title and Copyright Pages Only).

Famulok et al., "Stereospecific Recognition of Tryptophan Agarose by in Vitro Selected RNA," J. Am. Chem. Soc., 114:3990–3991 [1992].

Haseloff and Gerlach, "Simple RNA enzymes with new and highly specific endoribonuclease activities," Nature 334:585–591 [1988].

Hille, *Ionic Channels of Excitable Membranes*, Sinauer Associates Inc., Massachusetts, pp. 341–345 [1992].

Hirano et al., "Distribution of Saccharide Residues on Membrane Fragments from a Myeloma–Cell Homogenate: Its Implications for Membrane Biogenesis," Proc. Natl. Acad. Sci. USA 69:2945–2949 [1972].

Hu and Messing, "The making of strand–specific M13 probes," Gene 17:271–277 [1982].

Jefferies et al., "A catalytic 13–mer ribozyme," Nucl. Acids Res., 17:1371–1377 [1989].

Jellinek et al., "Inhibition of Receptor Binding by High–Affinity RNA Ligands to Vascular Endothelial Growth Factor," Biochemistry 83:10450–10456 [1994].

Kacian et al., "A Replicating RNA Molecule Suitable for a Detailed Analysis of Extracellular Evolution and Replication," *Proc. Natl. Acad. Sci. USA* 69:3038–3042 [1972].

Kessler (ed.), *Non–Radioactive Labeling and Detection of Biomolecules*, pp. 93–144, Springer–Verlag, Berlin [1992].

Kim et al., "Three–dimensional model of the active site of the self–splicing rRNA precursor of *Tetrahymena*," Proc. Natl. Acad. Sci. USA 84:8788–8792 [1987].

Kincka (ed.), *Nonisotopic DNA Probe Techniques*, Academic Press, San Diego, CA [1992]; Title and Copyright pages could not be obtained at this time, but would be provided at a later time should the Examiner desire a copy.

Langer et al., "Enzymatic synthesis of biotin–labeled polynucleotides: Novel nucleic acid affinity probes," Proc. Natl. Acad. Sci. USA 78:6633–6637 [1981].

Lohse et al., "Ribozyme–catalysed amino–acid transfer reactions," Nature 381:442–444 [1996].

Lorsch et al., "In Vitro Selection of RNA Aptamers Specific for Cyanocobalamin," Biochemistry 33:973–982 [1994].

McConn et al., "Investigations of the Chymotrypsini–catalyzed Hydrolysis of Specific Substrates," J. Biol. Chem., 246:2918–2925 [1971].

Milligan et al., "Synthesis of Small RNAs Using T7 RNA Polymerase," Meth. Enzymol., 180:51–62 [1989].

Moore et al., "Site–Specific Modification of Pre–mRNA: The 2'–Hydroxyl Groups at the Splice Sites," Science 256:992–997 [1992].

Neher, "Correction for Liquid Junction Potentials in Patch Clamp Experiments," Meth Enzymol., 207:123–131 [1992].

Nielsen et al., "Peptide nucleic acids (PNAs): potential antisense and anti–gene agents," Anticancer Drug Des 8:53–63 [1993].

Remington's Pharmaceutical Sciences 18th ed., Mack Publishing Co, Easton Pa. (1990) (Title and Copyright Pages Only).

Roberts et al., "RNA–peptide fusions for the in vitro selection of peptides and proteins," Proc. Natl. Acad. Sci. 94:12297–12302 [1997].

Sambrook et al., *Molecular Cloning: A Laboratory Manual*, Cold Spring Harbor Press, NY, pp. 7.39–7.52, and 9.31–9.58 [1989].

Sassanfar et al., "An RNA motif that binds ATP," Nature 364:550–553 [1993].

Talvenheimo et al., "Reconstitution of Neurotoxin–stimulated Sodium Transport by the Voltage–sensitive Sodium Channel Purified from Rat Brain," J. Biol. Chem., 257:11868–11871 [1982].

Tamkun et al., "The Sodium Channel from Rat Brain," J. Biol. Chem., 259:1676–1688 [1984].

Tuerk et al., "In vitro evolution of functional nucleic acids: high–affinity RNA ligands of HIV–proteins," Gene 137:33–39 [1993].

Uebele et al., "Functional Differences in Kv1.5 Currents Expressed in Mammalian Cell Lines Are Due to the Presence of Endogenous Kvβ2.1 Subunits," J. Biol. Chem., 271:2406–2412 [1996].

Westley, in Grayson (ed.), *Antibiotics, Chemotherapeutics, and Antibacterial Agents for Disease Control*, pp. 301–318, John Wiley and Sons, New York [1982].

Wu and Wallace, "The Ligation Amplification Reaction (LAR)–Amplification of Specific DNA Sequences Using Sequential Rounds of Template–Dependent Ligation," Genomics 4:560–569 [1989].

Zhang et al., "Peptide bond formation by in vitro selected ribozymes," Nature 390:96–100 [1997].

Vlassov et al., "Transport of oligonucleotides across natural and model membranes," Biochim. Biophys. Acta 1197: 95–108 [1994].

Kabanov et al., "DNA Complexes with Polycations for the Delivery of Genetic Material into Cells," *Bioconjugate Chem.*, 6: 7–20 [1995].

Saberwal et al., "Cell–lytic and antibacterial peptides that act by perturbing the barrier function of membranes: facets of their conformational features, structure–function correlations and membrane–perturbing abilities," *Biochim. Biophys. Acta* 1997: 109–131 [1994].

Majerfeld et al., "An RNA pocket for an aliphatic hydrophobe," *Struc. Biol.*, 1: 287–292 [1994].

Majerfeld et al., "Isoleucine: RNA sites with associated coding sequences," *RNA* 4: 471–478 [1998].

Angelova et al., "Lipophilic compounds in biotechnology—interactions with cells and technological problems," *J. Biotech.*, 67: 13–32 [1999].

Gold et al., "Diversity of Oligonucleotide Functions," *Annu. Rev. Biochem.*, 64:761–797 [1995].

Yarus, "Amino Acids as RNA Ligands: A Direct–RNA Template Theory for the Code's Origin," *J. Mol. Evol.*, 47:109–117 [1998].

Jaeger et al., "Improved predictions of secondary structures for RNA," *Proc. Natl. Acad. Sci. USA* 86: 7706–7710 [1989].

Olovnikov, A. Towards the quantitative traits regulation: Fountain theory implications in comparative and developmental biology. Int. J. Dev. Biol. vol. 41(6):923–931, Dec. 1997.*

* cited by examiner

|     |                                                                      | liposome binding(%) | permeabilization |
|-----|----------------------------------------------------------------------|---------------------|------------------|
| #2  | UCUCGGAUGAU<u>GGGGGGGCGGG</u>UGUACCGCUAAUAUCUCUCGACACUUGU              | 2.5                 | −                |
| #10 | UCAAACA<u>GGGGGGGGG</u>UAACGACCAUUUUUGCGUGCUAUAAACAGUGGUG              | 12.9                | +                |
| #11 | CAUAGCCUAGUGGAACCGGUUAAGUCCCCAGGGUUGCGACGUAAAGUUGG                    | 16.3                | −                |
| #13 | ACUGACUUACGAGACUGUCUCGCCAAUUCCAGUGGGCCUGCGGAUCCUAA                    | 4.0                 | +                |
| #16 | CGCGCGAGCGGAUAC<u>GGGCGGGGGGGG</u>UUCACAGUGAUCCGUGAUUACCA              | 12.7                | +                |
| #22 | AACCUGAGCGGACAGCGGGCCCCACGCUCGCCUAAACGCUUAGCGCUUC                     | 15.0                | −                |
| #23 | GACUGGAGUGUUGCUAGUAGCUAAACCUUUCCCACUUAUAGUGGGUGCGGG                   | 12.0                | −                |
| #12 | GUGGUGUGCUGGGCUAUGGCUAUGUAACGAGUGACGAUUGGGAAUUAUCG                    | 8                   | +                |
|     |                                                                      |                     |                  |
| #8  | CUGUCUGGACUAGUCAAGUGCGCUAUUUAUCGUGUCAACCUUGGGGUGUG                    | 0.14                | −                |
| #3  | UUGCGCUGGGCCUCGUUUUACCCAGCGAAAGUAAUCCUGGGGGCUGAUGA                    | 0.16                | −                |
| #6  | UACUGAAUCUUAAUUCUGUGCGUGGUGAGGUCCCUGCUGUUGCGUUUAGU                    | 0.12                | −                |
| #14 | GACGACCUGAGAACCCGUUUUGCGACAGGAUGGCGGCUUUAUCAGGUUUA                    | 0.16                | −                |
| #15 | UCCCGGGCAGGUGCAUCCUACUUCUCUCCACUUACUCCACGCGGCUAUAC                    | 0.1                 | −                |
| #21 | UUUAUCUCUCUCGAGGGGUCUGACACUACGUAGGGGUAAUCGGUUUGGU                     | 0.1                 | −                |

FIG. 3 a
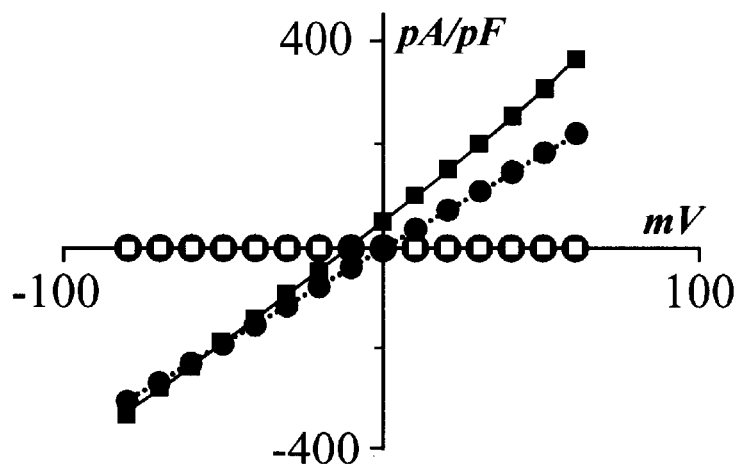
b
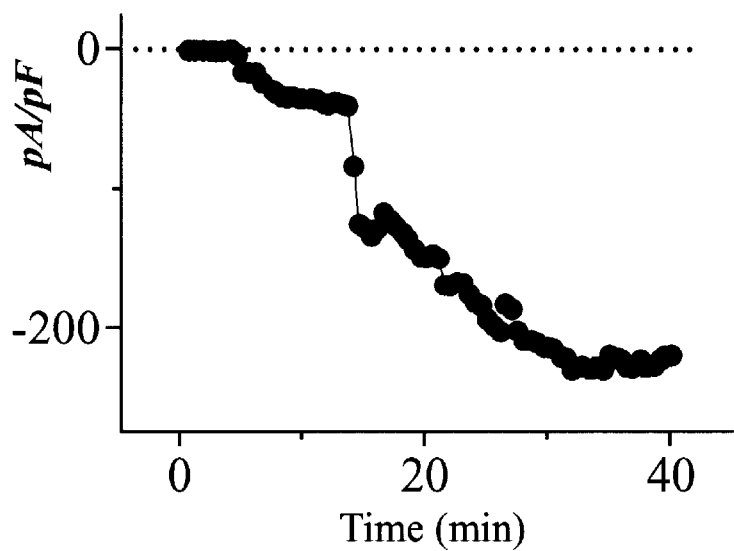
FIG. 6

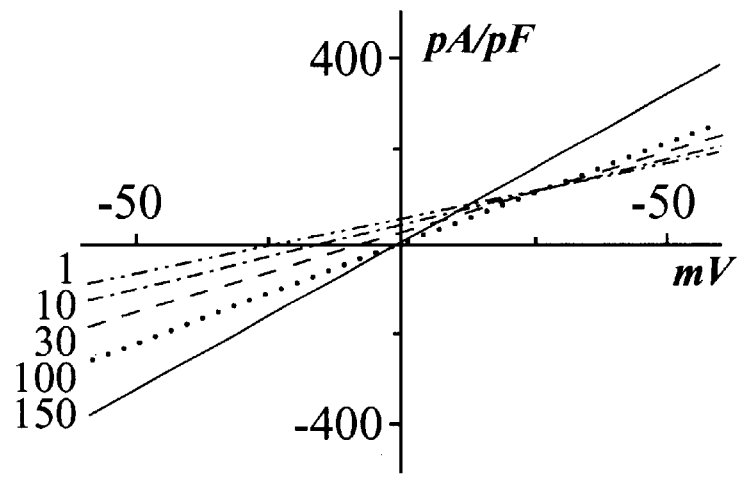
a
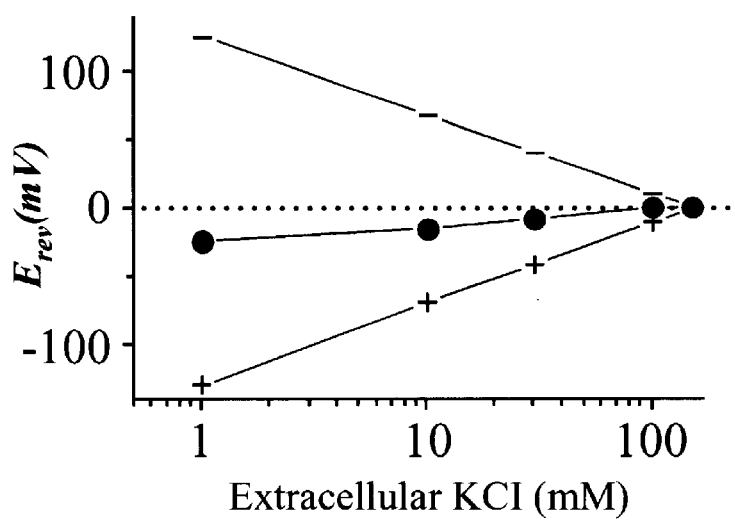
b
FIG. 7

US 6,225,063 B1

RNA CHANNELS IN BIOLOGICAL MEMBRANES

This application claims the benefit of U.S. Provisional Application No. 60/086,492, filed May 22, 1998.

The present invention was made with government support from the National Institutes of Health, Grant No. GM30881. The United States Government has certain rights in the invention.

FIELD OF THE INVENTION

The present invention relates to nucleic acid molecules capable of binding membranes, and more particularly RNA molecules capable of binding and forming channels in biological membranes.

BACKGROUND

The function of nucleic acids in living organisms is limited to a largely informational role. The "Central Dogma" of molecular biology, as postulated by Crick, proposes that deoxyribonucleic acid (DNA) serves as a template for the synthesis of other nucleic acids through replicative processes that "read" the information in template nucleic acids, and thus yield complementary nucleic acids, such as messenger ribonucleic acid (MRNA). mRNA then serves as a template for the translation of the information into proteins.

Most biological molecules do not specifically bind to nucleic acids. Some known exceptions are proteins (e.g., repressors, polymerases, activators, etc.) that function to transfer genetic information encoded in the nucleic acids into cellular structures and replicate genetic material. This binding depends upon the nucleotide sequence(s) that comprise the DNA or RNA involved. Short DNA sequences are known to bind to target proteins that repress or activate transcription in both prokaryotes and eukaryotes. Other short DNA sequences are known to serve as centromeres and telomeres of chromosomes, presumably by creating ligands for the binding of specific proteins that participate in chromosome mechanics.

RNA also binds some synthetic and regulatory proteins. For example, double-stranded RNA occasionally serves as a ligand for certain proteins, for example, the endonuclease RNase III from *E. Coli*. Proteins also bind to single-stranded RNA, although in these cases the single-stranded RNA often forms a complex three-dimensional shape that includes local regions of intramolecular double-strandedness. For example, the amino-acyl tRNA synthetases bind tightly to tRNA molecules with high specificity. As another example, a short sequence of RNA binds to the bacteriophage T4-encoded DNA polymerase. Thus, some RNA and DNA sequences are known to serve as binding partners for specific protein targets. Most known DNA binding proteins bind specifically to double-stranded DNA, while most RNA binding proteins recognize single-stranded RNA, although exceptions occur.

Nucleic acids are generally thought to have a limited range of biological activity as compared to proteins. However, some nucleic acids are known to bind target molecules other than those needed for transcription, translation and replication, and some have catalytic activity. For example, ribozymes are RNA molecules with enzymatic activity that is capable of repeatedly cleaving other RNA molecules in a nucleotide base sequence-specific manner. Such enzymatic RNA molecules can be targeted to virtually any RNA transcript, and efficient cleavage achieved in vitro (Kim et al., PNAS 84:8788 [1987]; Haseloff and Gerlach, Nature 334:585 [1988]; Cech, J. Amer. Med. Assoc., 260:3030 [1988]; and Jefferies et al., Nucl. Acids Res., 17:1371 [1989]). Ribozymes can catalyze the hydrolysis of RNA phosphodiester bonds in trans (and thus can cleave other RNA molecules) under physiological conditions. In general, enzymatic nucleic acids act by first binding to a target RNA. This binding occurs through the target binding portion of a enzymatic nucleic acid which is held in close proximity to an enzymatic portion of the molecule that acts to cleave the target RNA. Thus, the enzymatic nucleic acid first recognizes, and then binds a target RNA through complementary base-pairing, and once bound to the correct site, acts enzymatically to cut the target RNA. Strategic cleavage of such a target RNA destroys its ability to direct synthesis of an encoded protein. After an enzymatic nucleic acid has bound and cleaved its RNA target, it is released from that RNA and is available to bind and cleave a new target. This binding and cleavage process is then multiply repeated.

Some RNA and DNA molecules have also been proven to have the ability to bind various ligands, including amino acids (Famulok et al., J. Amer. Chem. Soc., 114:3990 [1992], Connell et al., Biochem., 32:5497 [1994]), nucleotides (Connell et al., Science 264:1137 [1994], Sassanfar et al., Nature 364:550 [1993]), antibiotics (Davies et al., In Gesteland and Atkins (eds.), *The RNA World*, p. 185, Cold Spring Harbor Press, NY [1993]), cyanocobalamin (Lorsch et al., Biochem., 33:973 [1994]), and proteins such as the reverse transcriptase, Rev and Tat proteins of HIV (Tuerk et al., Gene 137:33 [1993]), human nerve growth factor (Binkley et al., Nucl. Acids Res., 23:3198 [1995]), and vascular endothelial growth factor (Jellinek et al., Biochem., 83:10450 [1994]).

Drugs capable of interacting with membranes have found widespread use. Perhaps the most common class of drugs that interact with membranes are ionophores. Ionophores are lipid soluble compounds capable of binding and transporting specific ions through the cell membrane. Examples of ionophores include the calcium channel ionomycin, and the antimicrobials valinomycin and gramicidin. Valinomycin forms a lipid soluble complex with $K^+$ that readily passes through the mitochondrial membrane. Gramicidin induces the penetration of $K^+$, $Na^+$ and $H^+$ through the mitochondrial membrane, causing inhibition of oxidative phosphorylation. Other ionophore antimicrobials include nonactin, nigericin, lasalocid, and monensin (See Westley, inGrayson (ed.), *Antibiotics, Chemotherapeutics, and Antibacterial Agents for Disease Control*, p. 301–18, John Wiley and Sons, NY [1982]). Monensin and lasalocid are commonly used as animal feed supplements to reduce the occurrence of coccidiosis and other diseases and increase feed efficiency. However, as microorganisms often rapidly become resistant to antimicrobials, new antimicrobials are constantly under development.

What is needed is the identification of nucleic acids that can be utilized to alter membrane structure and finction, as well as target effector molecules to membranes of specific cell populations.

SUMMARY OF THE INVENTION

The present invention relates to nucleic acid molecules capable of binding membranes, and more particularly to RNA molecules capable of binding and forming channels in biological membranes. In accordance with the present invention, methods are contemplated for screening and isolating RNA molecules that bind, insert into, and/or permeabilize membranes, as well as compositions containing these molecules. The present invention also contemplates the use of nucleic acid molecules for various uses, including but not limited to altering the permeability of membranes, detectably labeling membranes, and targeting effector molecules to membranes. In particularly preferred embodiments of the present invention, the membranes are biological membranes.

In one embodiment, the present invention provides methods for screening nucleic acid molecules that bind to membranes, comprising: providing a composition comprising at least one nucleic acid molecules, and a membrane preparation; combining the composition and membrane preparation under conditions such that binding can occur, so as to produce a membrane with bound nucleic acid; and isolating said nucleic acid molecules bound to said membrane preparations. In some embodiments, the membranes that bind the nucleic acid molecules are characterized. In yet other embodiments, the nucleic acid molecules bound to the membrane preparation are purified. In other embodiments, the purified nucleic acid molecules are then amplified, cloned, and sequenced.

It is not intended that the present invention be limited to any certain type of nucleic acid molecule, as various nucleic acid molecules will find use in the present invention. In some embodiments of the present invention, the nucleic acid molecules are double-stranded or single-stranded RNA, while in other embodiments, the nucleic acid molecules are double-stranded or single-stranded DNA. In other embodiments, the nucleic acid molecules are hybrids of DNA and RNA, while in still other embodiments, the nucleic acids include protein nucleic acids (PNA). Thus, it is not intended that the present invention be limited to any particular nucleic acid, combination of nucleic acids, or complex between nucleic acid and another composition. The present invention is also not limited to any particular source of nucleic acid molecules. In some embodiments, the nucleic acid molecules are naturally occurring (e.g., isolated from a cell lysate or prepared from a cDNA library). In yet other embodiments of the present invention, the nucleic acid molecules are non-naturally occurring (i.e., chemically synthesized random sequences). In some embodiments, the nucleic acid molecules contain modified phosphodiester bonds (e.g., phosphorothioate, phosphoramidite, and methyl phosphate derivatives). In still other embodiments, the nucleotide subunits are modified to contain a detectable label (e.g., radioactive, enzymatic, fluorescent, luminescent labels, etc.).

In addition, the nucleic acid molecules of the present invention are not limited to any particular length. In some embodiments of the present invention, the nucleic acid molecules are from about 10 to 2500 nucleotides in length. In other embodiments, the nucleic acid molecules are from about 20 to 500 nucleotides in length. In still other embodiments, the present invention provides nucleic acid molecules from about 30 to 150 nucleotides in length. In further embodiments, the nucleic acid molecules are from about 40 to 120 nucleotides in length. In some preferred embodiments, the nucleic acids are from about 50 to 100 nucleotides in length. In a particularly preferred embodiment, the nucleic acid molecules are about 70 to 95 nucleotides in length, while in other particularly preferred embodiments, the nucleic acid molecules are about 50 to 60 nucleotides in length. It will be recognized that the nucleic acids of the present invention may also be included as a domain or portion of a larger nucleic acid molecule.

It is not intended that the methods and compositions of the present invention be limited to the use of any particular membrane preparation. Indeed, various membrane preparations are contemplated. In one embodiment of the present invention, the membrane preparation comprises liposomes. In another embodiment, the membranes comprise biological membranes (e.g., from cells or organelles). In further embodiments of the present invention, the biological membranes are provided as whole cells. In other embodiments, the biological membranes are from multiple types of cells. In yet other embodiments, the present invention provides biological membranes from a single cell type.

The present invention further provides compositions comprising nucleic acid molecules purified by methods comprising: providing a composition comprising nucleic acid molecules, and a membrane preparation; combining the composition and the membrane preparation under conditions such that binding of the nucleic acid molecules to the membrane can occur; isolating the nucleic acid molecules bound to the membrane preparations; and purifying the nucleic acid molecules bound to the membrane preparation.

The present invention further provides compositions comprising nucleic acid molecules capable of binding membranes. In one embodiment, the nucleic acid molecules are RNA molecules characterized as being insertable into a membrane bilayer, while in another embodiment, the nucleic acid molecules are DNA molecules characterized as being insertable into a membrane bilayer. In other embodiments of the present invention, the nucleic acid molecules are capable of hybridizing to RNA or DNA molecules of the present invention under medium to high stringency conditions. In a preferred embodiment, the nucleic acid molecules are selected from at least one of SEQ ID NOS:1–8. In still other embodiments, the nucleic acid molecules are isolated from cells.

In other embodiments, the present invention provides the above-identified nucleic acid molecules bound to or inserted into membranes. In further embodiments of the present invention, the nucleic acid molecules bound to or inserted into membranes form channels in membranes.

In further embodiments, the present invention provides compositions comprising nucleic acid molecules capable of binding membranes, wherein the nucleic acid molecules are conjugated or linked to at least one effector molecule or domain. It is not intended that the present invention be limited by the nature of the effector molecule. A variety of effector molecules or domains are contemplated including organic molecules (e.g., biotin), RNA molecules, DNA molecules, toxins (e.g., ricin or restrictocin), growth factors, cytokines, kinases, hormones, antibodies, and other proteins with a desired biological activity. In other embodiments, the effector molecule or domain targets the nucleic acid to a specific cell or organelle type. A variety of such targeting effector domains are contemplated, including, but not limited, to ligands for cell surface receptors, antigen binding proteins directed to cell surface proteins, and RNA and DNA oligonucleotides or polynucleotides capable of binding to cell surface proteins. It is contemplated that utilization of a targeting domain will facilitate targeting of particular cells of interest (e.g., hepatic cells, tumor cells, neurons, etc.).

In some embodiments, the present invention also provides methods for targeting effector molecules to membranes, comprising: providing a membrane preparation, and a composition comprising nucleic acid molecules, wherein the nucleic acid molecules are capable of binding to the membrane, and the nucleic acid molecules are linked to an effector domain; and combining the membrane preparation and nucleic acid molecule such that the nucleic acid molecules bind to membrane preparations.

In other embodiments, the present invention provides methods for altering the permeability of membranes, comprising the steps of providing a membrane preparation, and a composition comprising nucleic acid molecules, wherein the nucleic acid molecules are capable of binding to the membrane; and combining the membrane and composition such that the nucleic acid molecules bind to membrane preparation, and at least one membrane channel is formed in said membrane preparation. The nucleic acid molecules and membrane preparations contemplated by this method are described above. In a preferred embodiment, the nucleic acid molecules employed in this method are selected from SEQ ID NOS:1–8.

It is not intended that the present invention be limited by the selectivity of the membrane channels. In some embodiments of the present invention, the nucleic acid membrane channels allow the passage of multiple types of molecules. In other embodiments, the nucleic acid membrane channels allow the passage of at least one type of molecule. In particularly preferred embodiments, the channels allow passage of the molecules selected from sodium ions, calcium ions, potassium ions, chloride ions, and magnesium ions. In a particularly preferred embodiment, the nucleic acid membrane channel allows the passage of only one type of molecule.

The present invention also provides methods for labeling membranes, comprising: providing a membrane preparation, and a composition comprising nucleic acid molecules, wherein the nucleic acid molecules are detectably labeled and are capable of binding the membrane preparation; exposing the composition to the membrane preparation such that binding occurs, and detecting the labelled nucleic acid molecules It is not intended that the present invention be limited to the method of detecting said detectably labeled nucleic acid molecules. A variety of detecting means are contemplated. In one embodiment detection is accomplished by means of autoradiography (e.g., the nucleic acid is labelled with $P^{32}$). In yet another embodiment, detection is accomplished by means of fluorescence (e.g., rhodamine or fluorescein is used as a label) or chemiluminescence (e.g., horseradish peroxidase is used as a label).

BRIEF DESCRIPTION OF THE FIGURES

FIG. 3 shows certain RNA sequence binding percentages and channel forming ability after 11 cycles of selection. In this Figure, Gs are bold, while G clusters are underlined. Liposome binding is indicated as the % RNA coeluted with liposomes normalized to RNA eluted from the column (10 min. incubation at room temperature using 100 pM RNA with 20 μl liposomes (20 mg/ml phosphatidylcholine, 3 mg/ml cholesterol)). "Permeability positive" means induced current within 30 min. after 2 μM RNA was added to HEK 293 cells. The sequences shown in this Figure are SEQ ID NOS:1–8 (corresponding to #2 through #12, respectively; i.e., the first group of sequences), and SEQ ID NOS:11–16 (corresponding to #8 through #21, respectively; i.e., the second group of sequences).

FIGS. 6a and 6b show induction of ionic currents by extracellular RNA. Panel A provides data for when the membrane potential of HEK 293 cells was first held at −80 mV then varied in 10 mV increments to +60 mV, 20 min. after RNA (3–5 μM) addition to the cell bath. Currents in pA are normalized to membrane capacitance in pF to control for cell size. In this Figure, data are shown for control cell (○), random RNA (□), RNA after 11 selection cycles (●), mixture of 14 RNAs (■). Panel B provides the time course of current at −80 mV, induced by the mixture of 14 individual RNAs.

FIGS. 7a and 7b show ion selectivity of isolate 13 RNA. Panel A shows the current-voltage curves with variable extracellular KCl, recorded at 15 min. after RNA, normalized for membrane area. Panel B shows the dependence of reversal potential on KCl, with data for observed (●), and values calculated for completely cation (+), or anion specific (−) channels.

Definitions

Figure 1:
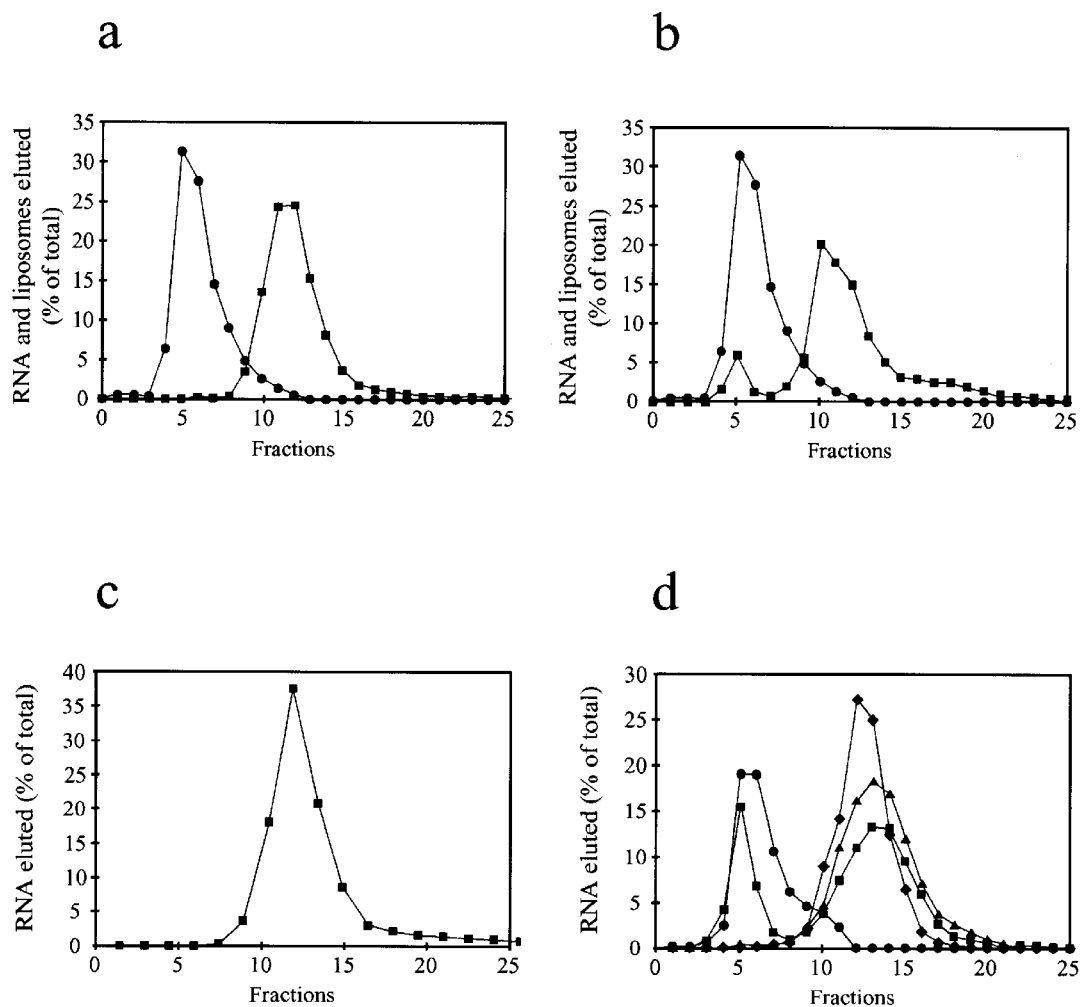
FIGS. 1a–1d in general show elution of RNA and liposomes from SEPHACRYL S-1000 column. Panel A shows randomized RNA (■) binding to liposomes (●); Panel B shows RNA (■) and liposomes (●) binding after the $8^{th}$ selection; Panel C shows RNA after $8^{th}$ selection (■) elution from SEPHACRYL® SF-100 column in the absence of liposomes; and Panel D shows dependence of RNA and liposome binding after the $11^{th}$ selection (●) in the presence of 20 mM $MgCl_2$ and 10 mM $CaCl_2$ (■), only 20 mM $MgCl_2$ (♦), and only 10 mM $CaCl_2$ (▲).

To facilitate understanding the invention, a number of terms are defined below.

As used herein, the term "eukaryote" refers to organisms distinguishable from "prokaryotes." It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s). This is in contrast to "non-selective binding," whereby interactions are arbitrary and not based on structural compatibilities of the molecules.

As used herein, the term "membrane" refers to, in one sense, a sheet or layer of material. It is intended that the term encompass all "biomembranes" or "biological membranes" (i.e., any organic membrane including, but not limited to, plasma membranes, nuclear membranes, organelle membranes, and synthetic membranes). In general, "biological membranes" comprise a continuous double layer of lipid molecules, in which various membrane proteins are embedded. Membrane lipid molecules are typically amphipathic, and most spontaneously form bilayers when placed in water. There are three major classes of lipid molecules in the plasma membrane bilayer, namely phospholipids, cholesterol, and glycolipids. In many cases, the lipid compositions of the inner and outer monolayers are different. In addition, the different membranes of a single eukaryotic cell have distinct lipid compositions. Typically, in addition to lipids, membranes are composed of proteins, glycolipids, steroids, sterols and/or other components. As used herein, the term "membrane fragment" refers to any portion or piece of a membrane. The term "polymerized membrane" refers to membranes that have undergone partial or complete polymerization.

As used herein, the term "polymerization" encompasses any process that results in the conversion of small molecular monomers into larger molecules consisting of repeated units. Typically, polymerization involves chemical crosslinking of molecular monomers to one another.

As used herein, the term "phospholipid membrane" refers to any structure composed of phospholipids aligned such that the hydrophobic heads of the lipids point one way while the hydrophilic tails point the opposite way. Examples of phospholipid membranes include the lipid bilayer surrounding cells and liposomes.

As used herein, the term "phospholipid membrane preparation" refers to any composition in which phospholipid membranes comprise at least a portion of the preparation. Examples of phospholipid membrane preparations include compositions containing cell lysates, cell culture, liposomes with or without other chemicals (e.g. buffers), cells located in vivo, and tissue culture. The term "membrane preparation" refers to any composition in which membranes comprise at least a portion of the preparation.

As used herein, the term "vesicle" refers to a small enclosed structures. Often the structures are membranes composed of lipids, proteins, glycolipids, steroids or other components associated with membranes. Vesicles can be naturally generated (e.g., the vesicles present in the cytoplasm of cells that transport molecules and partition specific cellular functions) or can be synthetic (e.g., liposomes).

As used herein, the term "liposome" refers to vesicles that are bounded by a lipid bilayer membrane. In particularly preferred embodiments, liposomes are artificially produced spherical lipid complexes that can be induced to segregate out of aqueous media. The term "glycoliposomes" refers to liposomes containing carbohydrates. The phrase "two-component glycoliposome" refers to glycoliposomes comprising two distinct chemical entities (e.g., carbohydrate linked lipids and lipids with polar head groups).

As used herein, the term "lipid sheet" refers to a region of lipid material that provides a surface for receptor/ligand interactions. A lipid sheet may comprise monolayer and bilayer films or may be present within three-dimensional assemblies such as liposomes, micelles, tubules, coils, rods, or other forms.

As used herein, the term "micelle" refers to a particle of colloidal size that has a hydrophilic exterior and hydrophobic interior.

As used herein, the term "ligands" refers to any ion, molecule, molecular group, or other substance that binds to another entity (e.g., receptor) to form a larger complex. Examples of ligands include, but are not limited to, peptides, carbohydrates, nucleic acids, antibodies, or any molecules that bind to receptors.

As used herein, the term "head group" refers to the molecular group present at the ends of molecules (e.g., the carboxylic acid group at the end of fatty acids).

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the terms "lipid-based materials" and "lipid assemblies" refers to any material that contains lipids. In some embodiments, "lipid assemblies" are structures including, but not limited to vesicles, liposomes, films, micelles, dendrimers, monolayers, bilayers, tubules, rods, and coils. As used herein, the term "lipid monomer" refers to a single lipid molecule. Lipid monomers include lipids that are covalently or otherwise attached to ligands or other chemical groups. In some embodiments, lipid monomers contain polymerizable groups.

As used herein, the term "surface exposed" refers to molecules that are present (e.g., accessible to receptor/ligand interactions) at the surface of a structure (e.g., a lipid assembly).

As used herein, the term "cloning" refers to the production of a compound or genetic sequence using recombinant technology. In particular, the term refers to the formation of clones or exact genetic replicas of the starting material.

As used herein, the term "purified" or "to purify" refers to the removal of contaminants from a sample.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein, the term "sequencing" refers to determining the nucleotide sequence of a nucleic acid molecule. Examples of sequencing techniques include Maxim-Gilbert chemical sequencing and Sanger dideoxy chain termination sequencing.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "nucleic acid molecule" refers to any nucleic acid containing molecule including, but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Nucleic acid molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA to an RNA of the present invention, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$(% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g. hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., PNAS 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (See e.g., Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural MRNA produced by the embryo to form duplexes. These duplexes then block either the further transcription of the MRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural or synthetic source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "nucleic acid sequence" refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence. "Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al., Anticancer Drug Des 8:53–63 [1993]).

As used herein, "deletion" is defined as a change in either nucleotide or amino acid sequence in which one or more nucleotides or amino acid residues, respectively, are absent.

As used herein, an "insertion" or "addition" is that change in a nucleotide or amino acid sequence which has resulted in the addition of one or more nucleotides or amino acid residues, respectively, as compared to, naturally occurring sequences.

As used herein, a "substitution" results from the replacement of one or more nucleotides or amino acids by different nucleotides or amino acids, respectively.

As used herein, the term "purified" (or "purify") refers to the removal of contaminant(s) from a sample. As used herein, the term "substantially purified" refers to molecules (e.g., nucleic or amino acid sequences), that are removed from their natural environment, isolated or separated, and are at least 60% free, preferably 75% free, and most preferably 90% free from other components with which they are naturally associated.

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Variants can often be tested in functional assays, as known in the art.

The term "recombinant DNA molecule" as used herein refers to a DNA molecule that is comprised of segments of DNA joined together by means of molecular biological techniques.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39–7.52 [1989]).

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

A "composition comprising a given polynucleotide sequence" as used herein refers broadly to any composition containing the given polynucleotide sequence. The composition may comprise an aqueous solution.

The term "antigen binding protein" as used herein refers to proteins which bind a specific antigen. "Antigen binding proteins" include, but are not limited to, immunoglobulins, polyclonal, monoclonal, chimeric, single chain, humanized antibodies, Fab fragments, F(ab')2 fragments, and Fab expression libraries The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the regulation of Ras mediated signal transduction pathways.

As used herein, the term "ribonucleoprotein" refers to a complex macromolecule containing both RNA and protein.

As used herein, the term "derivative" refers to the chemical modification of a nucleic acid encoding a particular structure. Illustrative of such modifications would be replacement of hydrogen by an alkyl, acyl, or amino group. A nucleic acid derivative would encode a polypeptide which retains essential biological characteristics of naturally-occurring a protein or its subunits.

As used herein, the term "biologically active" refers to molecules or peptides having structural, regulatory, or biochemical functions of a naturally occurring molecules or peptides. Likewise, "immunologically active," defines the capability of the natural, recombinant, or synthetic proteins or any oligopeptide thereof, to induce a specific immune response in appropriate animals or cells, and to bind with specific antibodies.

As used herein, "affinity purification of ribonucleoprotein particles" refers to the purification of ribonucleoprotein particles, through the use of an "affinity oligonucleotide" (i.e., an antisense oligonucleotides) to bind the particle, followed by the step of eluting the particle from the oligonucleotide by means of a "displacement oligonucleotide." In the present invention, the displacement oligonucleotide has a greater degree of complementarity with the affinity oligonucleotide, and therefore produces a more thermodynamically stable duplex than the particle and the affinity oligonucleotide. Under sufficiently mild conditions, the method results in the enrichment of functional ribonucleoprotein particles.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DESCRIPTION OF THE INVENTION

The present invention relates to nucleic acid molecules capable of binding membranes (e.g., biological membranes), and more particularly to RNA molecules capable of binding and forming channels in membranes. In this regard, the present invention provides methods of screening nucleic acid molecules that bind membranes. The present invention also provides compositions comprising nucleic acid molecules capable of binding membranes, as well as methods in which these compositions are used to alter the permeability of, and/or detectably label membranes. In each of the embodiments of the invention, and in particular, the preferred embodiments, the membranes are biological membranes.

A. Screening for Nucleic Acids that Bind to Membranes

The present invention contemplates screening nucleic acids for their ability to bind membranes using a modification of the SELEX procedure. The basic SELEX procedure is described in U.S. Pat. Nos. 5,475,096; 5,270,163; and 5,475,096; and in PCT publications WO 97/38134, WO 98/33941, and WO 99/07724, all of which are herein incorporated by reference. The SELEX procedure allows identification of a nucleic acid molecules with unique sequences, each of which has the property of binding specifically to a desired target compound or molecule.

Briefly, the SELEX procedure involves selection from a mixture of candidates in step-wise iterations. The SELEX procedure starts with a mixture of nucleic acids, preferably comprising a segment of randomized sequence. The mixture is contacted with a target under conditions favorable for binding. Next, unbound nucleic acids are partitioned from those nucleic acids which have bound to target molecules. Then, the nucleic acid-target pairs are dissociated and the nucleic acid is either amplified or isolated to yield a preparation enriched for target binding. The steps of binding, partitioning, dissociating and amplifying may be reiterated through as many cycles as desired.

Nucleic acids that have the highest affinity constants for the target are most likely to bind. After partitioning, dissociation and amplification, a second nucleic acid mixture is generated that is enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved upon repetition of the cycle. The method may be used to sample as many as about $10^{18}$ different nucleic acid species in a test mixture. The nucleic acids of the test mixture preferably include a randomized sequence portion, as this portion provides a large number of possible sequences and structures with a wide range of binding affinities for a given target. A nucleic acid mixture comprising, for example a 20 nucleotide randomized segment can have $4^{20}$ candidate possibilities. However, the present invention is not limited to a randomized segment of any particular length. In some embodiments, the randomized portion may be from about 40 to 120 base pairs in length, while in other embodiments, the randomized portion may be from about 50 to 100 base pairs in length, and in some preferred embodiments, the randomized portion is from about 70 to 90 base pairs in length.

The randomized portion is flanked by 5' and 3' fixed sequence regions. The fixed sequence regions are conserved sequences useful for efficient amplification (e.g., by PCR). Accordingly, the same pair of PCR primers can be utilized to amplify the randomized regions selected by the protocol. In some preferred embodiments, the fixed sequence regions are designed so that dimer formation and annealing between primers is minimized. In other preferred embodiments, the fixed regions include a promoter region (e.g., T3, T7, or SP6 promoter). In still other embodiments, the 5' fixed sequence region and 3' fixed sequence region are flanked by restriction sites to allow easy cloning of the entire nucleic acid including the fixed regions, or subcloning of the randomized region. Useful restriction sites include, but are not limited to, sites known in the art such as EcoRI, Hind III, Pst I, etc.

Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations. Partitioning methods used in SELEX rely on a partitioning matrix. High affinity oligonucleotides may be separated using various methods, including chromatographic-type processes, binding to nitrocellulose filters, liquid-liquid partition, gel filtration, and density gradient centrifugation.

Accordingly, the present invention contemplates screening a randomized pool of nucleic acid molecules for the ability to bind to membranes. In some embodiments, a composition comprising nucleic acids is provided. In some embodiments, the mixture comprises greater than about $10^{12}$ different nucleic acid sequences, while in particularly preferred embodiments, the mixture comprises greater than about $10^{18}$ different nucleic acid sequences. In preferred embodiments of the present invention, the nucleic acids include a randomized portion. In other embodiments, the randomized portion is from about 30 to 150 nucleotides in length. In still other embodiments, the randomized portion is from about 40 to 120 nucleotides in length. In other preferred embodiments, the randomized portion is from about 50 to 100 nucleotides in length. In some particularly preferred embodiments, the randomized portion is from about 70 to 95 nucleotides in length, while in other particularly preferred embodiments, the randomized portion is from about 50 to 60 nucleotides in length. However, it is not intended that the nucleic acids of the present invention be limited to the sequences identified by this method. It will be recognized that the nucleic acids of the present invention, and especially the randomized proteins of the nucleic acids of the present invention, may also be included as a domain or portion of a larger nucleic acid molecule.

In further embodiments of the present invention, a preparation comprising membranes is provided. In some embodiments, membranes are preferably in the form of liposomes. In other embodiments, the membranes are biological membranes (e.g., from cells or organelles).

In some embodiments of the present invention, the nucleic acids and membrane are combined so that the nucleic acids bind to or are inserted into the membranes to form a nucleic acid/membrane binding complex. In some preferred embodiments, $Ca^{++}$ (about 5–15 mM, most preferably about 10 mM) is included to ensure and/or optimize binding.

In some embodiments of the present invention, the fraction containing the nucleic acid/membrane binding complex is separated from the nucleic acid/membrane preparation mixture. In particularly preferred embodiments, the separation is accomplished by gel filtration (e.g., using a SEPHACRYL S-1000 (Pharmacia) column).

In still further embodiments of the present invention, a fraction of nucleic acids enriched for membrane binding is recovered or isolated from the nucleic acid/membrane binding complex. In some embodiments, the nucleic acids are chloroform extracted and ethanol precipitated. In other embodiments, the selected RNA fraction is then reverse transcribed (e.g., with AMV reverse transcriptase), priming with an oligonucleotide that anneals to the 3' constant region of the RNA. In still further embodiments, the cDNA produced from this reverse transcription is amplified with primers that anneal to the 3' and 5' constant regions. In some embodiments, RNA for the next selection cycle is then generated by in vitro transcription using an RNA polymerase (e.g., T7 polymerase) that recognizes the promoter in the constant region. In other embodiments, the RNA is purified. For example, denaturing polyacrylamide gels (e.g., SDS-PAGE) may be used, along with standard procedures for UV shadowing and gel elution, for this purification step.

In other embodiments, the combining, binding, separating and isolating steps are repeated on each successive membrane-binding nucleic acid-enriched fraction until no significant increase in binding is achieved upon repetition of the cycle. In other embodiments, about 1000 pmol of the nucleic acid is incubated with the membranes for about four cycles, while about 100 pmol the nucleic acid is incubated with the membranes for about seven additional cycles.

In still further embodiments of the present invention, the isolated nucleic acids are amplified and cloned. In some embodiments, the cloned nucleic acids are sequenced.

B. Identification of Nucleic Acids that Bind to Membranes

The present invention provides nucleic acid molecules which bind or insert into membranes (e.g., biological membranes). While an understanding of the mechanism of the present invention is not necessary to successfully practice the invention, it is believed that nucleic acid molecules with particular sequences bind to sites on membranes. Membranes (e.g. liposomes and cell membranes) are composed of a phospholipid bilayer. Certain phospholipids composed of glycerol and fatty acids, are also composed of a cationic choline moiety called phosphatidylcholine. It is also believed that phosphatidylcholine serves as a surface target for certain nucleic acid molecules.

In some embodiments of the present invention, the nucleic acid molecules are RNA molecules identified by the variation of the SELEX procedure described above. After the screening steps are completed, the selected RNAs are isolated (e.g., by chloroform/phenol extraction and precipitation). Preferably, the isolated RNAs are reverse transcribed to cDNA, amplified, and cloned as known in the art (See e.g., Ciesiolka et al., Meth. Enzymol., 267:315 [1996]). The RNA molecules of the present invention may then be transcribed from the cloned cDNA via the promoter (e.g., T7, T3, or SP6 promoter) in the fixed sequence region using methods known in the art (See e.g., Milligan et al., Meth. Enzymol., 180:51 [1989]). Alternatively, the RNAs may be chemically synthesized. In some particularly preferred embodiments of the present invention, the RNAs are selected from SEQ ID NOS:1–8.

In other embodiments, the present invention provides cDNA molecules complementary to the RNA molecules identified by the variation of the SELEX procedure described above. The cDNA molecules may be obtained from any suitable source (e.g., synthesized by PCR, chemically synthesized, or isolated from plasmids by restriction digestion). The DNA molecules of the present invention may be single-stranded or double-stranded. Single-stranded DNA molecules complementary to the RNA molecules described above may be synthesized following subcloning and expression of the cDNA from a suitable vector, as known in the art (e.g., M13, see Messing et al., Gene 17:271 [1982]). Additionally, in some embodiments, the nucleic acids include the fixed sequence region, while in other embodiments, the fixed sequence region is removed.

In still other embodiments, the present invention provides nucleic acid molecules which hybridize under medium to high stringency conditions to the RNA and DNA molecules described above. It is contemplated that the RNA molecules described above may serve as the starting point for the directed evolution of nucleic acid molecules with desired functions (e.g., binding to a particular subset of cell types (e.g., tumor cells, hepatic cells or neurons), selective ion permeability, increased ion permeability, or selective disruption of microbial cell membranes). In methods for directed evolution, random mutations are introduced into the nucleic acid, and nucleic acids with increased functionality are selected. The mutations may be introduced (preferably to the randomized portion) by performing PCR under mutagenic conditions (Bartel et al., Science 261:1411–18 [1993]; Beaudry et al., Science 257:635–641 [1992]). It is also contemplated that nucleic acid molecules may be identified which insert into the membrane bilayer in a particular orientation. Such nucleic acid molecules could be used advantageously, to present conjugated or linked molecules to either the interior or exterior of a cell or organelle as desired.

The non-specific binding of relatively large nucleic acids (i.e., about 1500 bases) to phospholipid bilayers has been described (See e.g., Budker et al., FEBS Lett., 95:143–46 [1978]; Budker et al., Nucl. Acids Res., 8:2499–514 [1980]; Budker et al., Anti. Res. Dev., 2:177–84 [1992]). However, it is not intended that the present invention be limited to particular mechanism of action. Indeed, an understanding of the mechanism is not necessary to make and use the present invention. Nonetheless, it is believed that the mechanism of specific membrane binding by the nucleic acids of the present invention differs from the non-specific binding observed by Budker et al. First, the binding efficiency of the nucleic acids of the present invention is about 4–5 orders of magnitude greater than the binding efficiency observed by Budker et al. Second, the specific binding observed in the present invention requires $Ca^{++}$, while the apparently non-specific binding of Budker et al., does not require $Ca^{++}$. Third, the binding observed by Budker et al. was reversible upon the addition of EDTA, excess cold RNA, or monovalent ions. In contrast, the binding of the nucleic acids of the present invention is essentially irreversible. Fourth, the binding observed by Budker et al. did not induce membrane permeability, as was observed with the nucleic acids of the present invention. Fifth, the binding observed by Budker et al. increased the sensitivity of the nucleic acid to nucleases. In contrast, some of the nucleotides of the nucleic acids of the present invention are protected upon binding. Sixth, the binding observed by Budker et al. causes the aggregation of liposome preparations as indicated by increased turbidity. In contrast, the binding of the nucleic acids of the present invention does not induce aggregation of liposomes as visualized by electron microscopy.

C. Conjugation of Membrane Binding Domains to other Molecules

In order for many drugs and imaging agents to have therapeutic or diagnostic potential, it is necessary for them to be delivered to the proper location in the body or even more specifically, a cell. The present invention provides compositions and methods for targeting effector molecules to membranes (e.g., biological membranes, such as cellular and organelle membranes) by conjugating the nucleic acid molecules of present invention with effector molecules or domains. Various targeting strategies are known in the art, but these techniques do not employ nucleic acids to bind the cellular membranes. One approach is exemplified by U.S. Pat. No. 4,093,607, herein incorporated by reference, which describes antibodies conjugated to therapeutic agents and methods of employing these constructs in targeting specific cell or tissue antigens. Antibodies conjugated to therapeutic drugs are used to alter the distribution of the therapeutic agent so that it is concentrated at the target cells. Another approach to drug targeting is exemplified by U.S. Pat. No. 5,149,794, herein incorporated by reference, which describes the covalent binding of drugs to a lipid carrier. It is believed that this technique has the advantage of facilitating the entry of drugs that have been specifically targeted to certain cells.

The present invention provides nucleic acid molecules (capable of binding to specific types of cell or tissue membranes) that are conjugated with certain effector (e.g., drug) molecules. It is contemplated that the efficacy of certain drugs can be increased (or lower doses are needed to effect the same result) and that the availability of therapeutic agents to particular cells or tissue types can be increased. Accordingly, in some embodiments, the present invention provides conjugate molecules comprising a nucleic acid membrane binding domain and an effector domain. The effector domain may be a nucleic acid operably linked to the nucleic acid binding domain, or a protein or organic molecule covalently linked to the nucleic acid membrane binding domain.

In further embodiments of the present invention, the effector domain has a catalytic function. In some embodiments, the effector domain comprises a protein having kinase or phosphorylase activity. In other embodiments, the protein has an antioxidant activity (e.g., superoxide dismutase). In still further embodiments, the effector domain comprises an RNA with catalytic activity (i.e., a ribozyme). Ribozymes act by recognizing and then binding a target RNA through complementary base-pairing, and once bound to the correct site, act enzymatically to cut the target RNA. Strategic cleavage of such a target RNA will destroy its ability to direct synthesis of an encoded protein. Examples of ribozymes motifs with enzymatic activity include hammerheads and hairpins (See e.g., U.S. Pat. Nos. 5,891,684; 5,877,022; 5,869,253; 5,811,300; 5,795,778; 5,728,818; and 5,714,383, all of which are incorporated herein by reference).

In still other embodiments of the present invention, the effector domain has a targeting function. Accordingly, in some embodiments, the effector domain comprises an antigen binding protein that recognizes a cell surface or organelle specific antigen. In other embodiments, the effector domain comprises a ligand for a cell surface receptor. In still further embodiments, the effector domain comprises a signal peptide for a particular organelle. In still other embodiments, the effector domain comprises a ligand binding nucleic acid. Nucleic acids that bind proteins such as reverse transcriptase, Rev and Tat proteins of HIV (Tuerk et al., Gene 137:33 [1993]); human nerve growth factor (Binkley et al., Nucl. Acids Res., 23:3198–205 [1995]); and vascular endothelial growth factor (Jellinek et al., Biochem., 83:10450–6 [1994]), have been identified. In some embodiments of the present invention, the membrane binding nucleic acid is linked to both a catalytic effector domain and targeting effector domain.

When the nucleic acid membrane binding domain and effector domain are both of the same nucleic acid type (e.g., both are RNA or both are DNA), the domains may be operably linked so that only a single nucleic acid molecule need be synthesized. DNA molecules containing both an effector domain and nucleic acid membrane binding domain can be synthesized by PCR or excised from a plasmid by restriction digestion. RNA molecules containing both an effector domain and nucleic acid membrane binding domain can be produced by transcription of a template that encodes both domains (Burke et al., RNA 4:1165 [1998], incorporated herein by reference).

Protein effector domains can be conjugated to nucleic acids (See e.g. Lohse et al., Nature 381:442 [1996]; Zhang et al., Nature 390:96 [1997]; Roberts et al., PNAS 94:12297 [1997]). In some embodiments, a thiol or primary amino group is introduced on the 5' end of an RNA during transcription by an RNA polymerase (e.g., T7 RNA polymerase). In other embodiments, the nucleic acid can be reacted with N-bromoacetyl-N'-phenylalanyl-cystamine to convert the nucleic acid to a 5'-Phe-nucleic acid with a free amino group capable of functioning as an aminoacyl acceptor. Peptides and proteins can be conveniently attached to the thiol or amino group. In other embodiments, the 3' end of a nucleic acid may be modified to contain puromycin, which serves as an peptidyl receptor.

When the effector and nucleic acid membrane-binding domains are of different nucleic acid types (e.g., one is DNA and the other is RNA), the two may be joined together using a bridging oligonucleotide and T4 DNA or RNA ligase (See e.g., Moore et al., Science 256:992 [1992]). In this method, the bridging oligonucleotide is preferably about 20 base pairs in length, and shares a region of complementarity with each of the nucleic acids to be joined. The oligonucleotide hybridizes to each of the nucleic acids to align the ends so that the ligase can join them. This method may also be used to join two RNA molecules.

D. Uses of Nucleic Acids that Bind to Membranes

The nucleic acids provided by the present invention are suitable for a wide variety of uses. The nucleic acids alone can be used, or they can be conjugated to effector molecules as described above.

1. Use as Ion Channels

The present invention provides nucleic acid molecules that form channels in membranes. In this regard, the nucleic acids of the present invention are capable of altering the permeability of membranes (e.g., biological membranes). While an understanding of the mechanism is not necessary to practice the present invention, it is believed that insertion of nucleic acid molecules into the membrane alters the membrane structure to cause increased ion permeability. The nucleic acid molecules of the present invention may alter membrane structure by insertion from the surface of the proximal phospholipid leaflet.

In some embodiments of the present invention, nucleic acid molecules are provided that allow the passage of only certain ions (e.g., $Na^+$, $K^+$, $Ca^{++}$, and $Mg^{++}$). In other embodiments, nucleic acids which bind preferentially to one type of cell or tissue are provided. In this regard, the treatment of particular ion/ion channel related diseases (e.g., Liddle's syndrome, pseudohypoaldosteronism type I, cystic fibrosis, and pulmonary edema) is contemplated by administering the nucleic acid molecules of the present invention.

It is also contemplated that the nucleic acid molecules of the present invention will find use as selective ionophores (i.e., as ionophores targeting cell membranes of pathogenic organisms) to treat disease. Examples of ionophore antimicrobials include such compounds as valinomycin, gramicidin, nonactin, nigericin, lasalocid, and monensin. It is contemplated that RNA antibiotics that will cause increased ion permeability will be derived from the nucleic acids of the present invention.

2. Use for Targeting to Cell Membranes

It is also contemplated that nucleic acids of the present invention will find use in targeting the effector molecules described above to biological membranes. In some embodiments, the membrane binding nucleic acid serves as an "anchor" that is inserted into the cell membrane or membranes of organelles in eukaryotic cells (e.g., membranes of the mitochondria, endoplasmic reticulum, lysomes, and/or nuclei). In some embodiments, the membrane binding nucleic acid serves as an anchor, while a first effector domain linked to the nucleic acid provides cell or target specificity (e.g., an RNA binding motif, an antigen binding protein, or a receptor ligand) and a second effector domain linked to the nucleic acid provides a biological effect (e.g., a ribozyme).

In other embodiments, the present invention contemplates nucleic acid molecules capable of selectively binding biological membranes. For example, the present invention contemplates nucleic acid molecules capable of selectively binding the phospolipid membranes of certain types of tissues or cells, but not other types of tissues or cells. In this regard, certain types of cells or tissues can be monitored (e.g. by detectably labeling the cell membranes) for diagnostic purposes. Also in this regard, certain types of tissues or cells could be targeted for disease therapy. Selective targeting can also be employed to destroy specific cells (e.g. tumor cells or pathogenic organisms).

3. Use for Labeling Membranes

The nucleic acids of the present invention will also find use for detectably labelling biological membranes. In particular, various organelles (e.g., mitochondria, lysosomes, nuclei) with membranes may be visualized within eukaryotic cells. The labeled membrane binding nucleic acids may also be used to assess fusion between cells (e.g., following electrofusion or viral induced fusion), and changes in membrane fluidity and structure. In other embodiments, labeled nucleic acids that selectively bind to one cell type but not other cell types are used to discriminate between cells in a sample. In some embodiments of the present invention, the nucleic acids are synthesized so as to contain a modified base with a detectable label (See e.g., Kessler (ed.), *Non-Radioactive Labeling and Detection of Biomolecules*, Springer-Verlag, Berlin [1992]; Kincka (ed.) *Nonisotopic DNA Probe Techniques*, Academic Press, San Diego, Calif. [1992]). Examples of suitable labels include, but are not limited to, fluorescence, radioactive, luminescent, and enzymatic labels (e.g., rhodamine, fluorescein, alkaline phosphatase, horseradish peroxidase, silver, $^{32}P$, $^{35}S$, digoxygenin, etc.). Upon binding of the nucleic acid to the membrane, the labels may be detected by autoradiography, fluorography, chemiluminescence, fluorescence, silver enhancement or other suitable techniques. In other embodiments, the bases may be modified with a chemical group (e.g., biotin) (See e.g., Langer et al., PNAS 78:6633–37 [1981]), to facilitate indirect detection. For example, nucleic acids incorporating bases modified with biotin are commonly detected by the use of avidin conjugated to a detectable label (e.g., rhodamine, fluorescein, alkaline phosphatase, horseradish peroxidase, silver, $^{32}P$ or $^{35}S$).

E. Pharmaceutical Compositions of Nucleic Acids

The present invention contemplates in vivo and in vitro applications of the nucleic acid molecules described herein. Thus, the present invention relates to pharmaceutical compositions which may comprise all or portions of the nucleic acids of the present invention, and may be administered in any sterile, biocompatible pharmaceutical carrier, including, but not limited to, saline, buffered saline, dextrose, and water.

One problem encountered in the therapeutic use of nucleic acids is that oligonucleotides in their phosphodiester form may be quickly degraded in body fluids by intracellular and extracellular enzymes such as endonucleases and exonucleases, before the desired effect is manifest. However, certain chemical modifications of the nucleic acids of the present invention can be made to increase the in vivo stability of the nucleic acid or to enhance or to mediate delivery of the nucleic acid. Examples of nucleic acid modifications contemplated by the present invention include, but are not limited to, those which provide other chemical groups that incorporate additional charge, polarizability, hydrophobicity, hydrogen binding, electrostatic interaction, and functionality to the nucleic acid bases or to the nucleic acid as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations (e.g., the isobases isocytidine and isoguanidine) and the like. Modifications can also include 3' and 5' modifications such as capping.

The nucleic acids can be parenterally administered to the patient (e.g., intravenously) in a pharmaceutically acceptable carrier such as physiological saline. Standard methods for intracellular delivery of peptides can be used (e.g., delivery via liposomes). Such methods are well known to those of ordinary skill in the art. The formulations of this invention may also be administered using any other suitable method (e.g., subcutaneous, intramuscular, intraperitoneal, intrathecal, etc.).

As is well known in the medical arts, dosages for any one patient depends upon many factors, including the patient's size, body surface area, age, the particular compound to be administered, sex, time and route of administration, general health, and interaction with other concurrently administered drugs.

Accordingly, in some embodiments of the present invention, the nucleic acids can be administered to a patient alone, or in combination with other nucleotide sequences, drugs or hormones or in pharmaceutical compositions in which it is mixed with excipient(s) or other pharmaceutically acceptable carriers. In one embodiment of the present invention, the pharmaceutically acceptable carrier is pharmaceutically inert.

Depending on the condition being treated, these pharmaceutical compositions may be formulated and administered systemically or locally (techniques for formulation and administration may be found in the latest edition of "Remington's Pharmaceutical Sciences" [Mack Publishing Co, Easton Pa.]). Suitable routes may, for example, include oral or transmucosal administration; as well as parenteral delivery, including intramuscular, subcutaneous, intramedullary, intrathecal, intraventricular, intravenous, intraperitoneal, or intranasal administration.

The pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of the nucleic acid may be that amount which induces ionic inflow (e.g., when the nucleic is utilized as an ion channel), or results in the reduction of number of bacteria (e.g., when the nucleic acid is used as cationic amphiphilic drug). Determination of effective amounts is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffm, or liquid polyethylene glycol with or without stabilizers.

Compositions comprising a compound of the invention formulated in a pharmaceutical acceptable carrier may be prepared, placed in an appropriate container, and labeled for treatment of an indicated condition.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, and is combined with buffer prior to use.

For any compound used in the method of the invention, the therapeutically effective dose can be estimated initially from cell culture assays. Then, preferably, the dosage can be formulated in animal models (particularly murine models) to achieve a desirable circulating concentration range.

A therapeutically effective dose refers to that amount of nucleic acid which ameliorates symptoms of the disease state. Toxicity and therapeutic efficacy of such compounds can be determined by standard pharmaceutical procedures in cell cultures or experimental animals, eg, for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician on a patient-by-patient case. Dosage and administration are adjusted to provide sufficient levels of the active moiety or to maintain the desired effect. Additional factors that may be taken into account include the severity of the disease state; age, weight, and gender of the patient; diet, time and frequency of administration, drug combination(s), reaction sensitivities, and tolerance/response to therapy, etc. Long-acting pharmaceutical compositions might be administered every 3 to 4 days, every week, or once every two weeks, depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See U.S. Pat. Nos. 4,657,760; 5,206,344; and 5,225,212, all of which are herein incorporated by reference). Administration to the bone marrow may necessitate delivery in a manner different from intravenous injections. Thus, the compositions of the present invention will find use in various settings.

EXPERIMENTAL

The following examples are provided in order to demonstrate and further illustrate certain preferred embodiments and aspects of the present invention and are not to be read as limiting the scope thereof.

In the experimental disclosure which follows, the following abbreviations apply: ° C. (degrees Centigrade); bp (base pair); kb (kilobase pair); kD (kilodaltons); gm (grams); $\mu$g (micrograms); mg (milligrams); ng (nanograms); $\mu$l (microliters); ml (milliliters); mm (millimeters); nm (nanometers); $\mu$m (micrometer); M (molar); mM (millimolar); $\mu$M (micromolar); nM (nanomolar); U (units); V (volts); mV (millivolts); MW (molecular weight); mCi (millicurrie); $\mu$Ci (microcurrie); sec (seconds); min(s) (minute/minutes); hr(s) (hour/hours); ab and Ab (antibody); HCl (hydrochloric acid); $MgCl_2$ (magnesium chloride); KCl (potassium chloride); NaCl (sodium chloride); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); PAGE (polyacrylamide gel electrophoresis); Tris (tris (hydroxymethyl)aminomethane); EDTA (Ethylenediaminetetraacetic Acid); HEPES (4-(2-Hydroxyethyl)piperazine-1-ethanesulphonic acid; w/v (weight to volume); v/v (volume to volume); ATCC (American Type Culture Collection, Manassas, Va.); Gibco BRL (Gibco BRL, Gaithersburg, Md); and Sigma (Sigma Fine Chemical Co., St. Louis, Mo).

Example 1

Screening RNA Molecules For Ability to Bind Membranes

This example describes a screen for identifying nucleic acids that bind to membranes. To obtain RNA molecules capable of binding to lipid bilayers, a selection procedure was employed based on gel-filtration of phosphatidylcholine liposomes incubated with a pool of $10^{15}$ randomized RNA molecules. The initial RNA pool consisted of 95-nucleotide oligomer transcripts containing 50 central randomized positions, encoded within flanking PCR primer sequences containing a T7 promoter (5'CGGAAGCTTCTGCTACATGCAATGG (SEQ ID NO:9)-$N_{50}$-CACGTGTAGTATCCTCTCCCTATAGTGAGTCG TATTAGAATTCGC (SEQ ID NO:10)-3'). Approximately, $10^{15}$ molecules of 95-nucleotide RNA transcribed from $2 \times 10^{14}$ independently synthesized DNA templates (Milligan and Uhlenbeck, Meth. Enzymol., 180:51 (1989), herein incorporated by reference) were heated at 65° C. for 3 minutes and cooled to room temperature over 10 minutes. Liposomes, predominantly unilamellar, were prepared from phosphatidylcholine (1,2-dioleoyl-sn-Glycero-3-Phosphocholine): cholesterol 4:1(Avanti Polar Lipids Inc.) at a final concentration 20 mg/ml, using the Avanti Mini-Extruder, according to manufacturer's protocol. Liposomes were stored at 4° C. under argon for up to 2 weeks. Initial selection buffer (50 mM Hepes pH 7.0, 5 mM $MgCl_2$, 1 mM $CaCl_2$, 50 mM NaCl) was changed after 4 cycles of selection to 50 mM Mes pH 5.5, 20 mM $MgCl_2$, 10 mM $CaCl_2$, 100 mM NaCl, 40 mM KCl, 100 mM $MnCl_2$, 20 mM $ZnCl_2$, which appears to be more favorable for the selected activity.

For selections, RNA (1000 pmol (cycles 1–4), 100 pmol (cycles 5–11)) incubation with liposomes (20 (1 of 20 mg/ml) was performed at room temperature for 15 min. Bound RNA was captured by fractionation of liposomes into the void volume of a SEPHACRYL S-1000 column. To decrease nonspecific sorption, the column was presaturated with both liposomes and non-specific RNA. Fifty $\mu$l fractions were collected and the first two, containing the leading part of the liposome peak were pooled, chloroform extracted, precipitated and processed as described (Ciesiolka et al., Meth. Enzymol., 267:315 [1996]).

Initial randomized RNA had no detectable affinity for liposomes (FIG. 1A), but 15% of RNA migrated with liposomes after the eighth cycle of selection (FIG. 1B). This migration was dependent on RNA-liposome interactions; eighth cycle RNA alone eluted as a single included peak corresponding to its molecular weight (FIG. 1C). RNA-liposome binding requires both $Mg^{2+}$ and $Ca^{2+}$ ions (FIG. 1D). Binding was completely abolished by omission of either from the reaction buffer. Other divalent cations present during selection were dispensable. After the $11^{th}$ cycle of selection, approximately 30% of RNA migrated with liposomes (FIG. 1D), and no increase in binding was detected during the last two rounds. Rna from pool 11 were cloned and characterized (Table 1).

TABLE 1

| Isolate NO: | Liposome Binding % | Channel Activity |
|---|---|---|
| #2 (SEQ ID NO:1) | 2.5 | – |
| #10 (SEQ ID NO:2) | 12.9 | + |
| #11 (SEQ ID NO:3) | 16.3 | – |
| #13 (SEQ ID NO:4) | 4.0 | + |
| #16 (SEQ ID NO:5) | 12.7 | + |
| #22 (SEQ ID NO:6) | 15.0 | – |
| #23 (SEQ ID NO:7) | 12.0 | – |
| #12 (SEQ ID NO:8) | 8.0 | + |

Example 2

Phospholipid Surface Target for RNA Recognition

This example describes a possible mechanism for nucleic acid binding. However, it is to be noted that the present invention is not limited to any particular mechanism or mode of action. Accordingly, an understanding of the mechanism of binding is not necessary to practice the present invention.

In these experiments, RNA affinity to free choline was measured using [$^{14}$C]choline (Sigma) in a equilibrium gel-filtration assay (McConn et al., J. Biol. Chem., 246:2918 (1971). $K_d$ values for RNA-liposome binding were estimated from $K_d=k_{on}/k_{off}$. $K_{on}$ was estimated as the diffusion controlled rate ($k_{on}\approx 10^8 M^{-1} s^{-1}$). $k_{off}$ was estimated from the survival of the complex during storage after gel chromatography; $t_{1/2} \geq 20$ hr, $k_{off} \leq 10^{-5}$ sec$^{-1}$.

An evident liposomal surface target for RNA recognition is the cationic choline moiety of phosphatidylcholine. Indeed, $11^{th}$-round pool RNA did not detectably bind liposomes in the presence of the potential competitor, 5 mM choline (FIG. 2), while a similar cationic control, 5 mM ethanolamine, did not interfere with binding. From the comparison of phosphatidylcholine and ethanolamine, choline methyls may contribute to affinity. However, attempts to measure RNA binding to free choline were unsuccessful, indicating that $K_d$ is probably $<10^{-4}$. In contrast, the estimated $K_d$ for RNA-liposome binding is $10^{-12}–10^{-13}$M. This apparent difference in affinity suggests that several cholines, or choline plus other bilayer features, comprise the RNA site.

Additionally, RNA-liposome association appears to be only slightly reversible. After re-chromatography of isolate 13 RNA bound to liposomes, more than 80% of RNA remained associated even after 12 hours at room temperature (not shown). Thus, partial binding (FIG. 3) to liposomes does not necessarily indicate a weak RNA association. Low binding levels can also be due to alternative RNA conformations.

Example 3

Identification of Active Biding Site

Figure 4:
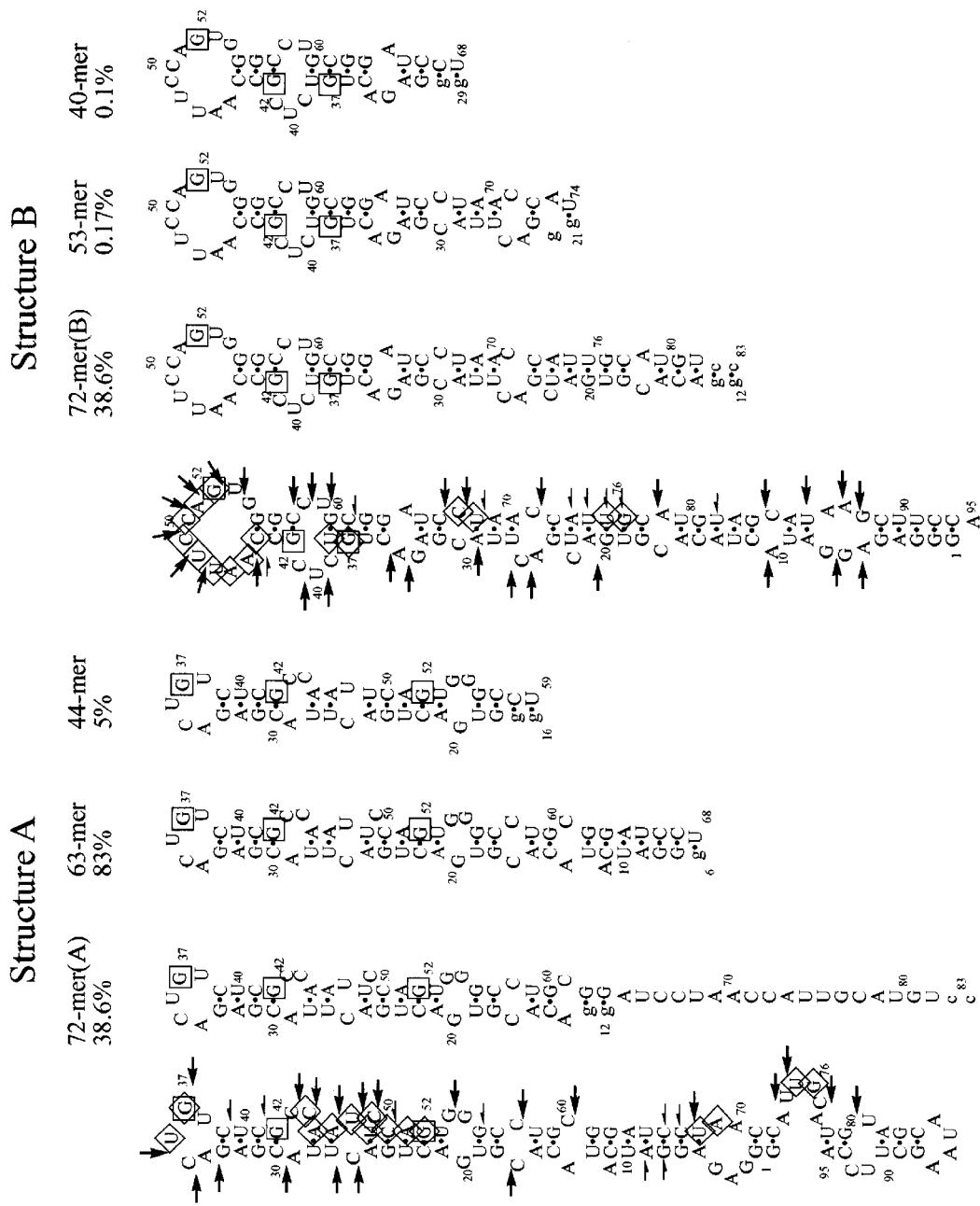
FIG. 4 shows truncation and binding by isolate 13 RNA. Structures A and B are two computed minimal free energy structures for isolate 13 RNA. Sites of RNA backbone flexibility ($Pb^{2+}$ cleavage) are indicated by arrows and half-arrows. Arrows are cleavage sites in agreement with the structure, while half-arrows indicate sites supporting the alternative conformation. Guanines protected from RNase T1 digestion are in squares. Nucleotides protected from nuclease S1 digestion are in rhombs. Nucleotides mutated to improve transcription are in small letters. Numbers are the fraction of RNAs bound normalized to concurrent experiments with full-sized, optimally folded isolate 13 RNA. The sequences shown in this Figure are SEQ ID NOS:17–24, for Structure A, as indicated from right to left; and SEQ ID NOS:25–32, for Structure B, as indicated from right to left. These Sequence ID numbers are assigned to each half of the structures shown in FIG. 4.

This example describes the determination of which confomer of isolate 13 has affinity to liposomes and the minimum active binding site for liposomes. Modeling of the secondary structure of isolate 13 RNA predicted two equally stable alternative structures (FIG. 4). Lead cleavage data is consistent with the existence of this RNA as an approximately equal mixture of these two secondary structures (A and B). In further support of conformational variation, slightly different folding conditions vary the fraction of bound isolate 13 RNA from 5 to 68% (not shown).

Variants of isolate 13 were then synthesized by in vitro transcription from either double stranded DNA obtained by PCR (72 and 64-mer) or directly from deoxyoligomers (for 53, 44 and 40 mers) (Milligan and Uhlenbeck, Meth. Enzymol., 180:51 [1989]). Additional 5' mutations were introduced to facilitate transcription.

Truncation of isolate 13 RNA suggests that only conformer A is active in binding (FIG. 4). First, 72-mer RNA, which can fold to both conformers, is partially active. Two truncated Rna (52- and 40-mer), that cannot fold to yield a variant of A, but readily fold into derivatives of structure B, were found to be completely inactive. On the other hand, truncated 64-mer RNA, designed to fold into structure A is 84% active. Further RNA truncation maintaining type A structure resulted in the 44-mer RNA that retains 5% activity.

Next, 5' labeled RNA bound to liposomes was isolated by gel filtration and digested with RNase T1 (Gibco BRL) at concentrations ranging between 0.025 U/µl and 0.2 U/µl for 1 minute at room temperature. RNase S1 (Gibco BRL) was used at concentrations ranging between 0.5 U/µl and 0.2 U/µl for 20 minutes at room temperature. Reactions were stopped by several phenol-chloroform extractions, then the RNA was ethanol precipitated and separated on 10% denaturing PAGE. Gels were quantitated using a BioRad phosphorimaging system.

Fifteen nucleotides were protected from SI nuclease digestion in liposome-bound RNA (FIG. 4). Such extensive protection is probably the sum of two different effects. First is the real protection of internucleotide bonds in the active conformer A upon binding ($U_{36}, G_{37}$). Second, the loss of S1 nuclease cuts unique to inactive conformer B in the liposome-bound fraction is expected (nucleotides 44–52).

Three G's ($G_{37}$, $G_{42}$, and $G_{52}$) are also significantly protected from digestion by T1 RNase upon liposome binding. These three residues are present in the active 44-mer. Thus the central, isolate 13-derived, 44 nucleotide hairpin contains an active region, and is thus far, the smallest structure competent for liposome binding.

Example 4

RNA Binding Alters Membrane Permeability in Liposomes

Permeability in artificial bilayers caused by RNA binding was evaluated in this Example by examining RNA-induced $^{22}$Na$^+$-efflux from the liposomes used for selection. Liposomes were loaded with 150 mM $^{22}$NaCl, incubated with RNA and applied to a DOWEX® column, which quantitatively adsorbs free Na$^+$. Liposomes loaded with $^{22}$NaCl were prepared by the detergent removal method previously described (Talvenheimo et al., J. Biol. Chem., 257:11868 [1982]). Dried mixtures of phosphatidylcholine and cholesterol (5:1) were dissolved in 20 mM Hepes pH 7.0, 150 mM NaCl, 20 mM MgCl$_2$, 10 mM CaCl$_2$ containing 10% TRITON® X-100 (octoxynol) (Sigma). The lipid solution was diluted with the same buffer, containing 10 mCi $^{22}$NaCl/ml, bringing the final concentrations of TRITON® X-100 (octoxynol) and phosphatidylcholine to 1.75% (w/v) and 1.7% (w/v), respectively. To remove TRITON® X-100 (octoxynol), the solution was incubated with BIO-BEADS® SM-2 (adsorbent). The amount of liposome-incorporated $^{22}$Na$^+$ was measured by dilution of 20 ml of a vesicle suspension loaded with $^{22}$NaCl in 200 (1 of 20 mM Hepes pH 7.0 with sucrose (Fisher)) varied to compensate the osmotic pressure. This was applied to a DOWEX® 50W-X8 column presaturated with 50 ml of liposomes. Liposomes were immediately eluted with 4 ml of Hepes-sucrose buffer. External $^{22}$Na$^+$ is adsorbed to the DOWEX® resin; $^{22}$Na$^+$ eluted from the column represents intravesicular $^{22}$Na$^+$. RNA-stimulated $^{22}$Na$^+$ efflux was measured by adding RNA to a 20-ml aliquot of a vesicle suspension loaded with $^{22}$NaCl (RNA concentration 5 mM; (100 molecules/liposome). Within liposomes, Na$^+$ is shielded from the resin and is detected at the column void volume. Channel activity therefore decreases $^{22}$Na$^+$ in column flow-through.

Figure 5:
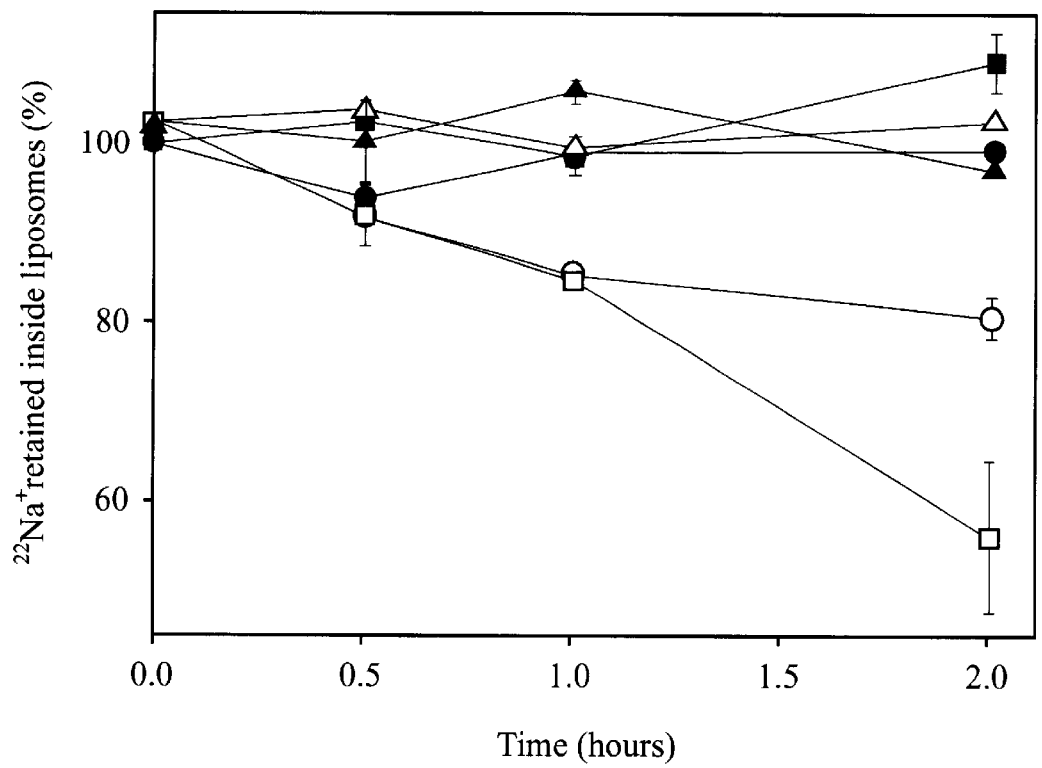
FIG. 5 shows RNA-induced $^{22}Na^+$ efflux from phosphatidylcholine:cholesterol liposomes, and time course for RNA-channel formation. This Figure shows the results for tests with no RNA (■), random RNA (●), isolate 13 (○), a mixture of 14 RNAs (□), a mixture of 14 RNAs in the absence of $Mg^{2+}$ and $Ca^{2+}$ (▲), and a mixture of 14 individual RNAs treated with NaOH (Δ). Each point is the mean of six samples derived from two independent experiments; the bars show SEM.

While neither random RNA nor hydrolyzed active Rna induced $^{22}$Na$^+$-efflux, a mixture of (SEQ ID NOS:1–8, and 11–16) induced approximately 45% efflux after 2 hours (FIG. 5). Pure isolate 13 RNA (SEQ ID NO:4) was also active. Sodium efflux was strictly dependent on the presence of Mg$^{2+}$ and Ca$^{2+}$. Although an understanding of the mechanism is not necessary in order to use the present invention, the common divalent requirement for both liposome binding and $^{22}$Na$^+$ efflux, supports an overlapping mechanism for both activities.

Maximum $^{22}$Na$^+$ efflux was achieved after 2 hours of RNA-liposome incubation (FIG. 5). Efflux was less than complete, perhaps due to the formation of internal membrane systems retaining $^{22}$Na$^+$, but inaccessible to externally-applied channels. The same limitation was observed with protein channels. For example, sodium channels from rat brain reconstituted into phosphatidylcholine liposomes release 35% of total $^{22}$Na$^+$ (Tanikun et al., J. Biol. Chem., 259:1676–88 [1984]). In contrast to binding experiments, where RNA appeared bound in less than a minute (not shown), channel formation assayed by $^{22}$Na$^+$ release seems to require a slower process (FIG. 5).

Example 5

RNA Binding Alters Permeability of Intact Cellular Membranes

Increased permeability of intact cellular membranes caused by RNA binding is described in this Example. Voltage clamp techniques were used to evaluate Rna applied to both external and internal faces of the human HEK293 plasma membrane.

Patch clamp recordings were made in HEK 293 cells (human epithelial kidney) cells from ATCC (ATCC Number: CRL-1573.1, using whole cell patch and inside-out patch configurations (Uebele et al., J. Biol. Chem., 271:2406 [1996]). HEK 293 cells were chosen for this experiment because it is a cell line with low endogenous currents frequently used to evaluate protein ion channel function. The bath solution for the patch clamp recordings contained 119 mM NaCl, 11 mM MgCl$_2$, 6.8 mM CaCl$_2$, 10 mM glucose, and 10 mM Hepes, pH 7.35. For whole cell recordings the pipette solution contained 110 mM KCl, 5 mM K$_4$BAPTA, 5 mM K$_2$ATP, 1 mM MgCl$_2$, and 10 mM Hepes, pH 7.2. For inside-out recordings the pipette solution contained 119 mM NaCl, 63.4 mM glucose, and 10 mM Hepes, pH 7.35. When the external KCl concentration was varied to measure ion selectivity, osmolarity was maintained with glucose. Junction potentials were measured with standard methods (See e.g., Neher, Meth Enzymol., 207:123 [1992]), using the patch-clamp amplifier in current-clamp mode. The junction potentials were less than ±12 mV. All voltages were corrected for junction potential error. Ion selectivity was estimated by comparing the $E_{rev}$ at variable external KCl concentrations to the $E_{rev}$ calculated from the Nernst equation (Hille, in Sunderland (ed.), *Ionic Channels of Excitable Membranes*, p. 341–45, Sinauer Associates Inc. [1992]).

Figure 2:
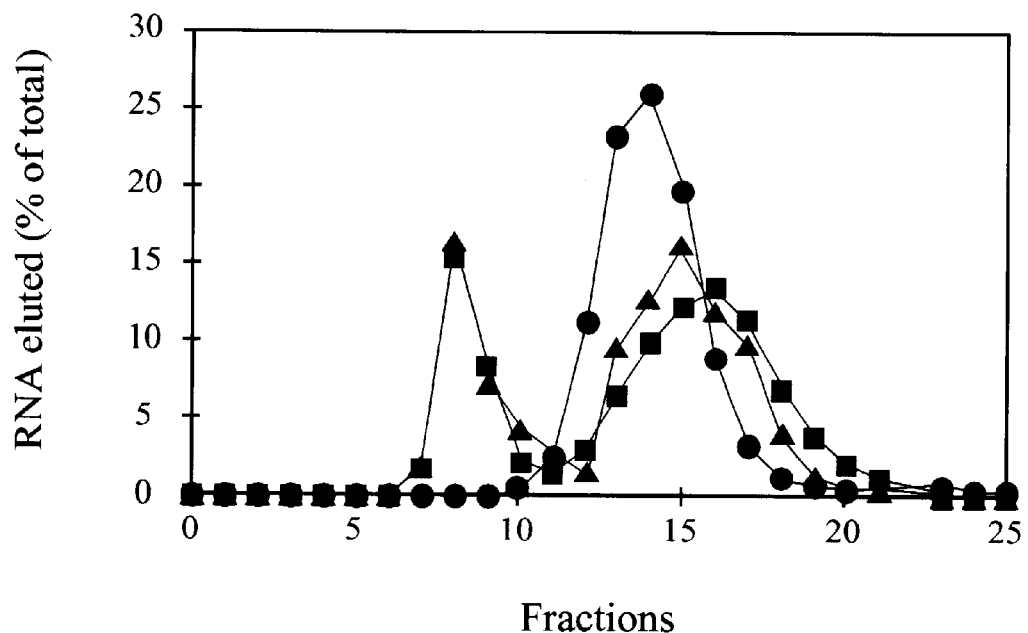
FIG. 2 shows elution of $11^{th}$ selection RNA from the SEPHACRYL S-1000 column after incubation with liposomes (■) in the presence of 5 mM choline (●), or in the presence of 5 mM ethanolamine (▲).

Randomized RNA sequences did not induce significant current (20 min at 5 mM) in whole cell patch mode. However, 11$^{th}$ cycle pool RNA induced nanoampere currents through the plasma membrane, with reverse potential around 0 mV (FIG. 2). An even larger effect was found with the mixture of 14 individual Rna (FIG. 6A). As for artificial bilayers, current through a cell membrane required high Mg$^{2+}$ and Ca$^{2+}$ (not shown).

Permeability effects are common; about 50% of individual liposome-binding Rna displayed channel-like activity (FIG. 2A). Somewhat as for liposomes, these effects on a real plasma membrane are slow, imposing a 5–10 minute lag, perhaps requiring binding and/or assembly of the active RNA within the membrane (FIG. 6B).

Inside-out patches, in which a small area of membrane is captured on the patch electrode, allow application of RNA to a plasma membrane's inner face. Plasma membranes are chemically asymmetric. Choline-containing phospholipids are selectively sorted to the outer leaflet (Bretscher, Science 181:622 [1973]), whereas glycolipids and glycoproteins, the carbohydrates of which might exclude macromolecules like RNA, are exclusively outside (Hirano et al., PNAS 69:2945 [1972]). Thus, an internal membrane face comprises a distinct RNA target. In fact, starting at 6 minutes after exposure of the internal membrane leaflet, isolate 13 (SEQ ID NO:4) RNA was found to increase ionic permeability of an inside-out patch. Action from inside and outside a human plasma membrane, taken together with activity on pure phospholipid bilayers, suggests that RNA will perturb many biological membranes.

Patch clamp measurements can also detect some types of specificity. Linear conductivity with a 0 mV reversal potential (FIG. 6A) suggests that the pool RNA yields voltage-independent conductivity and does not make a strong distinction among its permeant ions.

More particularly, variation of external KCl allowed assessment of the anion-cation specificity of a single RNA (FIG. 7). I–V curves for isolate 13 RNA-induced current (FIG. 7A) show a negative shift in reversal potential as external KCl decreases. FIG. 7B presents curves for outside KCl dependence of reversal potential calculated using the Nernst equation for cation and anion specific channels. Observed RNA activity appears to be weakly cation selective. Perhaps the overall negative potential on the RNA surface stabilizes cations more than anions.

From the above, it is evident that the present invention provides nucleic acid-based methods and compositions for binding and/or altering the permeability of membranes. In particular, the present invention provides nucleic acid-based methods and compositions for binding and/or altering the permeability of biological membranes.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

What is claimed is:

1. A composition comprising at least one nucleic acid molecule suitable for insertion into a biological membrane, wherein said nucleic acid molecule is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

2. The composition of claim 1, wherein said biological membrane comprises cell membranes.

3. The composition of claim 1, wherein said biological membrane comprises a phospholipid bilayer.

4. The composition of claim 1, wherein said at least one nucleic acid molecule comprises an RNA molecule.

5. The composition of claim 4, wherein said at least one nucleic acid molecule further comprises a nucleic acid molecule selected from the group consisting of DNA molecules complementary to said RNA molecule, and nucleic acid molecules capable of binding to said RNA and said DNA molecules.

6. The composition of claim 4, wherein said RNA molecule comprises synthetic RNA.

7. The composition of claim 1, wherein said at least one nucleic acid molecule is inserted into said biological membrane.

8. The composition of claim 7, wherein said nucleic acid molecule forms an ion channel in said biological membrane.

9. The method of claim 8, wherein said ion channel allows the passage of at least one molecule selected from the group consisting of sodium ions, calcium ions, potassium ions, chlorine ions and magnesium ions.

10. A method for altering membrane permeability comprising:
   a) providing;
      i) a membrane preparation, and
      ii) a composition comprising at least one nucleic acid molecule selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; and
   b) combining said membrane preparation and said composition, under conditions such that the membrane permeability of said membrane preparation is altered.

11. The method of claim 10, wherein said membrane preparation comprises cell membranes.

12. The method of claim 10, wherein said membrane preparation comprises a phospholipid bilayer.

13. The method of claim 10, wherein said at least one nucleic acid molecule comprises an RNA molecule.

14. The method of claim 13, wherein said RNA molecule comprises synthetic RNA.

15. The method of claim 13, wherein said at least one nucleic acid molecule further comprises a nucleic acid molecule selected from the group consisting of DNA molecules complementary to said RNA molecule, and nucleic acid molecules capable of binding to said RNA and said DNA molecules.

16. The method of claim 10, further comprising the step of forming at least one ion channel in said membrane preparation.

17. The method of claim 16, wherein said ion channel allows the passage of at least one molecule selected from the group consisting of sodium ions, calcium ions, potassium ions, chlorine ions and magnesium ions.

18. A method for labelling phospholipid membranes comprising ion channels, comprising:
   a) providing;
      i) a phospholipid membrane preparation, and
      ii) a composition comprising RNA molecules, wherein said RNA molecules are detectably labeled;
   b) exposing said composition to said phospholipid membrane preparation under conditions such that binding occurs, and produces labelled RNA molecules bound to said phospholipid membrane preparation, to produce labelled phospholipid membranes comprising ion channels.

19. The method of claim 18, wherein said RNA molecule is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

20. The method of claim 18, wherein said RNA molecules are from about 10 nucleotides to about 2500 nucleotides in length.

21. The method of claim 18, which further comprises a nucleic acid molecule selected from the group consisting of DNA molecules complementary to said RNA molecule, and nucleic acid molecules capable of binding to said RNA and said DNA molecules.

22. The method of claim 18, wherein said RNA molecule comprises synthetic RNA.

23. The method of claim 18, comprising the further step of c) detecting said labelled phospholipid membrane.

24. A method for forming an ion channel in a membrane, comprising:
   a) providing;
      i) a composition comprising at least one nucleic acid molecule selected from the group consisting of SEQ ID NO:1, SEQ ID NO:2, SEQ ID NO:3, SEQ ID NO:4, SEQ ID NO:5, SEQ ID NO:6 SEQ ID NO:7 and SEQ ID NO:8, and
      ii) a membrane preparation; and
   b) combining said composition and said membrane preparation under conditions such that said at least one nucleic acid molecule produces an ion channel in said membrane.

25. The method of claim 24, wherein said membrane preparation comprises cell membranes.

26. The method of claim 24, wherein said membrane preparation comprises a phospholipid bilayer.

27. The method of claim 24, wherein said ion channel allows the passage of at least one molecule selected from the group consisting of sodium ions, calcium ions, potassium ions, chlorine ions and magnesium ions.

28. The method of claim 24, wherein said at least one nucleic acid molecule comprises an RNA molecule.

29. The method of claim 28, wherein said at least one nucleic acid molecule further comprises a nucleic acid molecule selected from the group consisting of DNA molecules complementary to said RNA molecule, and nucleic acid molecules capable of binding to said RNA and said DNA molecules.

30. The method of claim 28, wherein said RNA molecule comprises synthetic RNA.

* * * * *

SEQUENCE LISTING

<160> NUMBER OF SEQ ID NOS: 32

<210> SEQ ID NO 1
<211> LENGTH: 50
<212> TYPE: RNA

```
<213> ORGANISM: Artificial Sequence
<220> FEATURE:
<223> OTHER INFORMATION: Description of Artificial Sequence: SYNTHETIC

<400> SEQUENCE: 1
ucucggauga ugggggggcg gguguaccgc uaauaucucu cgacacuugu                50

<210> SEQ ID NO 2
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 2
ucaaacaggg gggggguaac gaccauuuuu gcgugcuaua aacaguggug                50

<210> SEQ ID NO 3
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 3
cauagccuag uggaaccggu uaagucccca ggguugcgac guaaaguugg                50

<210> SEQ ID NO 4
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 4
acugacuuac gagacugucu cgccaauucc agugggccug cggauccuaa                50

<210> SEQ ID NO 5
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 5
cgcgcgagcg gauacgggcg ggggggguuc acagugaucc gugauuacca                50

<210> SEQ ID NO 6
<211> LENGTH: 49
<212> TYPE: RNA
<213> ORGANISM: Artificial Sequence
<220> FEATURE:
<223> OTHER INFORMATION: Description of Artificial Sequence: SYNTHETIC

<400> SEQUENCE: 6
aaccugagcg gacagcgggc cccacgcucg ccuaaacgcu uagcgcuuc                 49

<210> SEQ ID NO 7
<211> LENGTH: 51
<212> TYPE: RNA
<213> ORGANISM: Artificial Sequence
<220> FEATURE:
<223> OTHER INFORMATION: Description of Artificial Sequence: SYNTHETIC

<400> SEQUENCE: 7
gacuggagug uugcuaguag cuaaaccuuu cccacuuaua gugggugcgg g              51
```

```
<210> SEQ ID NO 8
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 8
guggugugcu gggcuauggc uauguaacga gugacgauug ggaauuaucg          50

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: SYNTHETIC

<400> SEQUENCE: 9
cggaagcttc tgctacatgc aatgg                                     25

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: SYNTHETIC

<400> SEQUENCE: 10
cacgtgtagt atcctctccc tatagtgagt cgtattagaa ttcgc               45

<210> SEQ ID NO 11
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 11
cugucuggac uagucaagug cgcuauuuau cgugucaacc uuggggugug           50

<210> SEQ ID NO 12
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 12
uugcgcuggg ccucguuuua cccagcgaaa guaauccugg gggcugauga           50

<210> SEQ ID NO 13
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 13
uacugaaucu uaauucugug cguggugagg ucccugcugu ugcguuuagu           50

<210> SEQ ID NO 14
<211> LENGTH: 50
<212> TYPE: RNA
<213> ORGANISM: Artificial Sequence
<220> FEATURE:
```

<223> OTHER INFORMATION: Description of Artificial Sequence: SYNTHETIC

<400> SEQUENCE: 14
gacgaccuga gaacccguuu ugcgacagga uggcggcuuu aucagguuua        50

<210> SEQ ID NO 15
<211> LENGTH: 50
<212> TYPE: RNA
<213> ORGANISM: Artificial Sequence
<220> FEATURE:
<223> OTHER INFORMATION: Description of Artificial Sequence: SYNTHETIC

<400> SEQUENCE: 15
ucccgggcag gugcauccua cuucucucca cuuacuccac gcggcuauac        50

<210> SEQ ID NO 16
<211> LENGTH: 49
<212> TYPE: RNA
<213> ORGANISM: Artificial Sequence
<220> FEATURE:
<223> OTHER INFORMATION: Description of Artificial Sequence: SYNTHETIC

<400> SEQUENCE: 16
uuuaucucuc ucgagggguc ugacacuacg uagggguaau cgguuuggu         49

<210> SEQ ID NO 17
<211> LENGTH: 45
<212> TYPE: RNA
<213> ORGANISM: Artificial Sequence
<220> FEATURE:
<223> OTHER INFORMATION: Description of Artificial Sequence: Synthetic

<400> SEQUENCE: 17
aagcuuccag ggagaggauc auacacguga cugacuuacg agacu             45

<210> SEQ ID NO 18
<211> LENGTH: 50
<212> TYPE: RNA
<213> ORGANISM: Artificial Sequence
<220> FEATURE:
<223> OTHER INFORMATION: Description of Artificial Sequence: Synthetic

<400> SEQUENCE: 18
uacgauguac guuaccaauc cuaggcgucc gggugaccuu aaccgcucug        50

<210> SEQ ID NO 19
<211> LENGTH: 45
<212> TYPE: RNA
<213> ORGANISM: Artificial Sequence
<220> FEATURE:
<223> OTHER INFORMATION: Description of Artificial Sequence: Synthetic

<400> SEQUENCE: 19
ccuguacguu accaauccua ggacacguga cugacuuacg agacu             45

<210> SEQ ID NO 20
<211> LENGTH: 47
<212> TYPE: RNA
<213> ORGANISM: Artificial Sequence
<220> FEATURE:
<223> OTHER INFORMATION: Description of Artificial Sequence: Synthetic

<400> SEQUENCE: 20
ccuguacguu accaauccua ggcguccggg ugaccuuaac cgcucug           47

<210> SEQ ID NO 21
<211> LENGTH: 31
<212> TYPE: RNA
<213> ORGANISM: Artificial Sequence
<220> FEATURE:
<223> OTHER INFORMATION: Description of Artificial Sequence: Synthetic

<400> SEQUENCE: 21
gggaucauac acgugacuga cuuacgagac u                          31

<210> SEQ ID NO 22
<211> LENGTH: 32
<212> TYPE: RNA
<213> ORGANISM: Artificial Sequence
<220> FEATURE:
<223> OTHER INFORMATION: Description of Artificial Sequence: Synthetic

<400> SEQUENCE: 22
uccuaggcgu ccggugacc uuaaccgcuc ug                          32

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic

<400> SEQUENCE: 23
gggugacuga cuuacgagac u                                     21

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic

<400> SEQUENCE: 24
uccgggugac cuuaaccgcu cug                                   23

<210> SEQ ID NO 25
<211> LENGTH: 49
<212> TYPE: RNA
<213> ORGANISM: Artificial Sequence
<220> FEATURE:
<223> OTHER INFORMATION: Description of Artificial Sequence: Synthetic

<400> SEQUENCE: 25
gggagaggau acuacacgug acugacuuac gagacugucu cgccaauuc       49

<210> SEQ ID NO 26
<211> LENGTH: 46
<212> TYPE: RNA
<213> ORGANISM: Artificial Sequence
<220> FEATURE:
<223> OTHER INFORMATION: Description of Artificial Sequence: Synthetic

<400> SEQUENCE: 26
accuucgaau acgauguacg uuaccaaucc uaggcguccg ggugac          46

<210> SEQ ID NO 27
<211> LENGTH: 38
<212> TYPE: RNA
<213> ORGANISM: Artificial Sequence
<220> FEATURE:
<223> OTHER INFORMATION: Description of Artificial Sequence: Synthetic -continued

```
<400> SEQUENCE: 27
ggacacguga ucgacuuacg agacugucuc gccaauuc                                    38

<210> SEQ ID NO 28
<211> LENGTH: 34
<212> TYPE: RNA
<213> ORGANISM: Artificial Sequence
<220> FEATURE:
<223> OTHER INFORMATION: Description of Artificial Sequence:  Synthetic

<400> SEQUENCE: 28
ccuguacguu accaauccua ggcguccggg ugac                                        34

<210> SEQ ID NO 29
<211> LENGTH: 28
<212> TYPE: RNA
<213> ORGANISM: Artificial Sequence
<220> FEATURE:
<223> OTHER INFORMATION: Description of Artificial Sequence:  Synthetic

<400> SEQUENCE: 29
gggacuuacg agacugucuc gccaauuc                                               28

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence:  Synthetic

<400> SEQUENCE: 30
uaccaauccu aggcguccgg gugac                                                  25

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence:  Synthetic

<400> SEQUENCE: 31
gggagacugu cucgccaauu c                                                      21

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence:  Synthetic

<400> SEQUENCE: 32
uccuaggcgu ccgggugac                                                         19
```